United States Patent
Kieval et al.

(10) Patent No.: US 7,840,271 B2
(45) Date of Patent: Nov. 23, 2010

(54) STIMULUS REGIMENS FOR CARDIOVASCULAR REFLEX CONTROL

(75) Inventors: Robert S. Kieval, Medina, MN (US);
Bruce J. Persson, Albertville, MN (US);
David J. Serdar, Shorewood, MN (US);
Peter T. Keith, St. Paul, MN (US)

(73) Assignee: CVRx, Inc., Minneapolis, MN (US)

( * ) Notice: Subject to any disclaimer, the term of this patent is extended or adjusted under 35 U.S.C. 154(b) by 1135 days.

(21) Appl. No.: 11/186,140

(22) Filed: Jul. 20, 2005

(65) Prior Publication Data

US 2005/0251212 A1 Nov. 10, 2005

Related U.S. Application Data

(60) Division of application No. 09/964,079, filed on Sep. 26, 2001, now Pat. No. 6,985,774, which is a continuation-in-part of application No. 09/671,850, filed on Sep. 27, 2000, now Pat. No. 6,522,926.

(51) Int. Cl.
*A61N 1/372* (2006.01)
(52) U.S. Cl. ........................................................ 607/44
(58) Field of Classification Search ................. 600/373, 600/377, 509; 607/2, 44, 116, 118
See application file for complete search history.

(56) References Cited

U.S. PATENT DOCUMENTS

| | | | |
|---|---|---|---|
| 3,309,924 A | 3/1967 | Kolin | |
| 3,421,511 A | 1/1969 | Schwartz et al. | |
| 3,522,811 A | 8/1970 | Schwartz et al. | |
| 3,593,718 A | 7/1971 | Krasner et al. | |
| 3,645,267 A | 2/1972 | Hagfors | |
| 3,650,277 A * | 3/1972 | Sjostrand et al. | 607/44 |
| 3,835,864 A | 9/1974 | Rasor et al. | |
| 3,870,051 A | 3/1975 | Brindley | |
| 3,943,936 A | 3/1976 | Rasor et al. | |
| 4,014,318 A | 3/1977 | Dockum et al. | |
| RE30,366 E | 8/1980 | Rasor et al. | |

(Continued)

FOREIGN PATENT DOCUMENTS

WO    WO 97/18856    5/1997

(Continued)

OTHER PUBLICATIONS

"Abstracts of the 40.sup.th Scientific Sessions", Supplement II to Circulation, vols. XXXV & XXXVI, Oct. 1967, II-253, 1 sheet.

(Continued)

*Primary Examiner*—Carl H Layno
*Assistant Examiner*—Frances P Oropeza
(74) *Attorney, Agent, or Firm*—Patterson Thuente Christensen Pedersen, P.A.

(57) ABSTRACT

Devices, systems and methods by which the blood pressure, nervous system activity, and neurohormonal activity may be selectively and controllably reduced by activating baroreceptors. A baroreceptor activation device is positioned near a baroreceptor, for example a baroreceptor in the carotid sinus. A control system may be used to modulate the baroreceptor activation device. The control system may utilize an algorithm defining a stimulus regimen which promotes long term efficacy and reduces power requirements/consumption.

16 Claims, 25 Drawing Sheets

U.S. PATENT DOCUMENTS

| | | |
|---|---|---|
| 4,256,094 A | 3/1981 | Kapp et al. |
| 4,323,073 A | 4/1982 | Ferris |
| 4,331,157 A | 5/1982 | Keller, Jr. et al. |
| 4,481,953 A | 11/1984 | Gold et al. |
| 4,525,074 A | 6/1985 | Murakami |
| 4,531,943 A | 7/1985 | Van Tassel et al. |
| 4,551,862 A | 11/1985 | Haber |
| 4,573,481 A | 3/1986 | Bullara |
| 4,586,501 A | 5/1986 | Claracq |
| 4,590,946 A | 5/1986 | Loeb et al. |
| 4,628,942 A | 12/1986 | Sweeney et al. |
| 4,640,286 A | 2/1987 | Thomson |
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Habor |
| 4,711,251 A | 12/1987 | Stokes |
| 4,719,921 A | 1/1988 | Chirife |
| 4,739,762 A | 4/1988 | Palmaz |
| 4,762,130 A | 8/1988 | Fogarty et al. |
| 4,762,820 A | 8/1988 | Gavras |
| 4,770,177 A | 9/1988 | Schroeppel |
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,819,662 A | 4/1989 | Heil, Jr. et al. |
| 4,825,871 A | 5/1989 | Cansell |
| 4,828,544 A | 5/1989 | Lane et al. |
| 4,830,003 A | 5/1989 | Wolff et al. |
| 4,832,038 A | 5/1989 | Arai et al. |
| 4,860,751 A | 8/1989 | Callaghan |
| 4,862,361 A | 8/1989 | Gordon et al. |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,917,092 A | 4/1990 | Todd et al. |
| 4,930,517 A | 6/1990 | Cohen et al. |
| 4,934,368 A | 6/1990 | Lynch |
| 4,940,065 A | 7/1990 | Tanagho et al. |
| 4,960,129 A | 10/1990 | dePaola et al. |
| 4,960,133 A | 10/1990 | Hewson |
| 4,967,159 A | 10/1990 | Manes |
| 4,969,458 A | 11/1990 | Wiktor |
| 4,972,848 A | 11/1990 | Di Domenico et al. |
| 4,987,897 A | 1/1991 | Funke |
| 5,010,893 A | 4/1991 | Sholder |
| 5,025,807 A | 6/1991 | Zabara |
| 5,031,621 A | 7/1991 | Grandjean et al. |
| 5,040,533 A | 8/1991 | Fearnot |
| 5,078,736 A | 1/1992 | Behl |
| 5,086,787 A | 2/1992 | Grandjean et al. |
| 5,092,332 A | 3/1992 | Lee et al. |
| 5,111,815 A | 5/1992 | Mower |
| 5,113,859 A | 5/1992 | Funke |
| 5,113,869 A | 5/1992 | Nappholz et al. |
| 5,117,826 A | 6/1992 | Bartelt et al. |
| 5,134,997 A | 8/1992 | Bennett et al. |
| 5,144,960 A | 9/1992 | Mehra et al. |
| 5,154,170 A | 10/1992 | Bennett et al. |
| 5,154,182 A | 10/1992 | Moaddeb |
| 5,158,078 A | 10/1992 | Bennett et al. |
| 5,170,802 A | 12/1992 | Mehra |
| 5,181,911 A | 1/1993 | Shturman |
| 5,199,428 A | 4/1993 | Obel et al. |
| 5,203,326 A | 4/1993 | Collins |
| 5,215,089 A | 6/1993 | Baker, Jr. |
| 5,222,971 A | 6/1993 | Willard et al. |
| 5,224,491 A | 7/1993 | Mehra |
| 5,243,980 A | 9/1993 | Mehra |
| 5,259,394 A | 11/1993 | Bens |
| 5,269,303 A | 12/1993 | Wernicket et al. |
| 5,282,468 A | 2/1994 | Klepinski |
| 5,282,844 A | 2/1994 | Stokes et al. |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,314,453 A | 5/1994 | Jeutter |
| 5,318,592 A | 6/1994 | Schaldach |
| 5,324,310 A | 6/1994 | Greeninger et al. |
| 5,324,325 A | 6/1994 | Moaddeb |
| 5,325,870 A | 7/1994 | Kroll et al. |
| 5,330,507 A | 7/1994 | Schwartz |
| 5,330,515 A | 7/1994 | Rutecki et al. |
| 5,331,966 A | 7/1994 | Bennett et al. |
| 5,335,657 A | 8/1994 | Terry et al. |
| 5,351,394 A | 10/1994 | Weinberg |
| 5,358,514 A | 10/1994 | Schulman et al. |
| 5,387,234 A | 2/1995 | Hirschberg |
| 5,408,744 A | 4/1995 | Gates |
| 5,411,540 A | 5/1995 | Edell et al. |
| 5,431,171 A | 7/1995 | Harrison et al. |
| 5,437,285 A | 8/1995 | Verrier et al. |
| 5,458,626 A | 10/1995 | Krause |
| 5,507,784 A | 4/1996 | Hill et al. |
| 5,509,888 A | 4/1996 | Miller |
| 5,522,854 A | 6/1996 | Ideker et al. |
| 5,522,874 A | 6/1996 | Gates |
| 5,529,067 A | 6/1996 | Larsen et al. |
| 5,531,766 A | 7/1996 | Kroll et al. |
| 5,531,778 A | 7/1996 | Maschino et al. |
| 5,531,779 A | 7/1996 | Dahl et al. |
| 5,535,752 A | 7/1996 | Halperin et al. |
| 5,540,734 A | 7/1996 | Zabara |
| 5,540,735 A | 7/1996 | Wingrove |
| 5,545,132 A | 8/1996 | Fagan et al. |
| 5,545,202 A | 8/1996 | Dahl et al. |
| 5,551,953 A | 9/1996 | Lattin et al. |
| 5,571,150 A | 11/1996 | Wernicke et al. |
| 5,575,809 A | 11/1996 | Sasaki |
| 5,578,061 A | 11/1996 | Stroetmann et al. |
| 5,593,431 A | 1/1997 | Sheldon |
| 5,634,878 A | 6/1997 | Grundei et al. |
| 5,643,330 A | 7/1997 | Holsheimer et al. |
| 5,645,570 A | 7/1997 | Corbucci |
| 5,651,378 A | 7/1997 | Matheny et al. |
| 5,680,590 A | 10/1997 | Parti |
| 5,683,430 A | 11/1997 | Markowitz et al. |
| 5,690,681 A | 11/1997 | Geddes et al. |
| 5,692,882 A | 12/1997 | Bozeman, Jr. et al. |
| 5,694,939 A | 12/1997 | Cowings |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,766,236 A | 6/1998 | Detty et al. |
| 5,766,527 A | 6/1998 | Schildgen et al. |
| 5,775,331 A | 7/1998 | Raymond et al. |
| 5,776,178 A | 7/1998 | Pohndorf et al. |
| 5,782,891 A | 7/1998 | Hassler et al. |
| 5,800,464 A | 9/1998 | Kieval |
| 5,807,258 A | 9/1998 | Cimochowski et al. |
| 5,810,735 A | 9/1998 | Halperin et al. |
| 5,814,079 A | 9/1998 | Kieval |
| 5,814,089 A | 9/1998 | Stokes et al. |
| 5,824,021 A | 10/1998 | Rise |
| 5,853,652 A | 12/1998 | Schildgen et al. |
| 5,861,012 A | 1/1999 | Stroebel |

| | | | | | | |
|---|---|---|---|---|---|---|
| 5,861,015 | A | 1/1999 | Benja-Athon | 6,701,176 B1 | 3/2004 | Halperin et al. |
| 5,876,422 | A | 3/1999 | van Groeningen | 6,701,186 B1 | 3/2004 | Spinelli et al. |
| 5,891,181 | A | 4/1999 | Zhu | 6,704,598 B2 | 3/2004 | Ding et al. |
| 5,895,416 | A | 4/1999 | Barreras, Sr. et al. | 6,748,272 B2 | 6/2004 | Carlson et al. |
| 5,904,708 | A | 5/1999 | Goedeke | 6,766,189 B2 | 7/2004 | Yu et al. |
| 5,913,876 | A | 6/1999 | Taylor et al. | 6,768,923 B2 | 7/2004 | Ding et al. |
| 5,916,239 | A | 6/1999 | Geddes et al. | 6,779,257 B2 | 8/2004 | Kiepen et al. |
| 5,919,220 | A | 7/1999 | Stieglitz et al. | 6,826,428 B1 | 11/2004 | Chen et al. |
| 5,928,272 | A | 7/1999 | Adkins et al. | 6,850,801 B2 | 2/2005 | Kieval et al. |
| 5,938,596 | A | 8/1999 | Woloszki et al. | 6,859,667 B2 | 2/2005 | Goode |
| 5,954,761 | A | 9/1999 | Machek et al. | 6,876,881 B2 | 4/2005 | Baumann et al. |
| 5,967,986 | A | 10/1999 | Cimochowski et al. | 6,894,204 B2 | 5/2005 | Dunshee |
| 5,967,989 | A | 10/1999 | Cimochowski et al. | 6,907,285 B2 | 6/2005 | Denker et al. |
| 5,987,352 | A | 11/1999 | Klein et al. | 6,922,585 B2 | 7/2005 | Zhou et al. |
| 5,987,746 | A | 11/1999 | Williams | 6,935,344 B1 | 8/2005 | Aboul-Hosn |
| 5,989,230 | A | 11/1999 | Frassica | 6,937,896 B1 | 8/2005 | Kroll |
| 5,991,667 | A | 11/1999 | Feith | 6,942,622 B1 | 9/2005 | Turcott |
| 6,006,134 | A | 12/1999 | Hill et al. | 6,942,686 B1 | 9/2005 | Barbut et al. |
| 6,016,449 | A | 1/2000 | Fischell et al. | 6,985,774 B2 | 1/2006 | Kieval et al. |
| 6,023,642 | A | 2/2000 | Shealy et al. | 7,010,337 B2 | 3/2006 | Furnary et al. |
| 6,050,952 | A | 4/2000 | Hakki et al. | 7,092,775 B2 | 8/2006 | Nomoto et al. |
| 6,052,623 | A | 4/2000 | Fenner et al. | 7,123,961 B1 | 10/2006 | Kroll et al. |
| 6,058,331 | A | 5/2000 | King | 7,139,607 B1 | 11/2006 | Shelchuk |
| 6,061,596 | A | 5/2000 | Richmond et al. | 7,146,226 B2 | 12/2006 | Lau et al. |
| 6,073,048 | A * | 6/2000 | Kieval et al. ............ 607/17 | 7,155,284 B1 | 12/2006 | Whitehurst et al. |
| 6,077,227 | A | 6/2000 | Miesel et al. | 7,158,832 B2 | 1/2007 | Kieval et al. |
| 6,077,298 | A | 6/2000 | Tu et al. | 7,192,403 B2 | 3/2007 | Russell |
| 6,104,956 | A | 8/2000 | Naritoku et al. | 7,194,313 B2 | 3/2007 | Libbus |
| 6,106,477 | A | 8/2000 | Miesel et al. | 7,225,025 B2 | 5/2007 | Goode |
| 6,110,098 | A | 8/2000 | Renirie et al. | 7,228,179 B2 | 6/2007 | Campen et al. |
| 6,115,628 | A | 9/2000 | Stadier et al. | 7,231,248 B2 | 6/2007 | Kramer et al. |
| 6,115,630 | A | 9/2000 | Stadier et al. | 7,236,821 B2 | 6/2007 | Cates et al. |
| 6,128,526 | A | 10/2000 | Stadier et al. | 7,236,861 B2 | 6/2007 | Paradis et al. |
| 6,141,588 | A | 10/2000 | Cox et al. | 7,286,878 B2 | 10/2007 | Stypulkowski |
| 6,141,590 | A | 10/2000 | Renirie et al. | 7,321,793 B2 | 1/2008 | Ben Ezra et al. |
| 6,161,029 | A | 12/2000 | Spreigl et al. | 2001/0003799 A1 | 6/2001 | Boveja |
| 6,161,047 | A | 12/2000 | King et al. | 2001/0020177 A1 | 9/2001 | Gruzdowich et al. |
| 6,178,349 | B1 | 1/2001 | Kieval | 2001/0023367 A1 | 9/2001 | King et al. |
| 6,178,352 | B1 | 1/2001 | Gruzdowich et al. | 2002/0005982 A1 | 1/2002 | Borlinghaus |
| 6,193,996 | B1 | 2/2001 | Effing et al. | 2002/0016548 A1 | 2/2002 | Stadier et al. |
| 6,205,359 | B1 | 3/2001 | Boveja | 2002/0026228 A1 | 2/2002 | Schaurte |
| 6,206,914 | B1 | 3/2001 | Soykan | 2002/0058877 A1 | 5/2002 | Baumann et al. |
| 6,208,894 | B1 | 3/2001 | Schulman et al. | 2002/0068897 A1 | 6/2002 | Jenkins et al. |
| 6,231,516 | B1 | 5/2001 | Keilman et al. | 2002/0072776 A1 | 6/2002 | Osorio et al. |
| 6,253,110 | B1 | 6/2001 | Brabec et al. | 2002/0072782 A1 | 6/2002 | Osorio et al. |
| 6,255,296 | B1 | 7/2001 | Daniels | 2002/0103516 A1 | 8/2002 | Patwardhan et al. |
| 6,266,564 | B1 * | 7/2001 | Hill et al. ............ 607/9 | 2002/0107553 A1 | 8/2002 | Hill et al. |
| 6,292,695 | B1 * | 9/2001 | Webster et al. ........ 607/14 | 2002/0128700 A1 | 9/2002 | Cross, Jr. |
| 6,292,703 | B1 | 9/2001 | Meier et al. | 2002/0151051 A1 | 10/2002 | Li |
| 6,324,421 | B1 | 11/2001 | Stadier et al. | 2002/0165586 A1 | 11/2002 | Hill et al. |
| 6,341,236 | B1 | 1/2002 | Osorio et al. | 2002/0183791 A1 | 12/2002 | Denker et al. |
| 6,371,922 | B1 | 4/2002 | Baumann et al. | 2003/0040785 A1 | 2/2003 | Maschino et al. |
| 6,393,324 | B2 | 5/2002 | Gruzdowich et al. | 2003/0050670 A1 | 3/2003 | Spinelli et al. |
| 6,397,109 | B1 | 5/2002 | Cammilli et al. | 2003/0060857 A1 | 3/2003 | Perrson et al. |
| 6,401,129 | B1 | 6/2002 | Lenander | 2003/0060858 A1 | 3/2003 | Kieval et al. |
| 6,415,183 | B1 | 7/2002 | Scheiner et al. | 2003/0078623 A1 | 4/2003 | Weinberg et al. |
| 6,438,409 | B1 | 8/2002 | Malik et al. | 2003/0093130 A1 | 5/2003 | Stypulkowski |
| 6,438,428 | B1 | 8/2002 | Axelgaard et al. | 2003/0100924 A1 | 5/2003 | Foreman et al. |
| 6,442,413 | B1 | 8/2002 | Silver | 2003/0120316 A1 | 6/2003 | Spinelli et al. |
| 6,442,435 | B2 | 8/2002 | King et al. | 2003/0149450 A1 | 8/2003 | Mayberg |
| 6,445,953 | B1 | 9/2002 | Bulkes et al. | 2003/0212440 A1 | 11/2003 | Boveha et al. |
| 6,473,644 | B1 | 10/2002 | Terry et al. | 2003/0229380 A1 | 12/2003 | Adams et al. |
| 6,522,926 | B1 | 2/2003 | Kieval et al. | 2004/0010303 A1 | 1/2004 | Bolea et al. |
| 6,564,101 | B1 | 5/2003 | Zikria | 2004/0019364 A1 | 1/2004 | Kieval et al. |
| 6,564,102 | B1 | 5/2003 | Boveja | 2004/0034391 A1 | 2/2004 | Baumann et al. |
| 6,584,362 | B1 | 6/2003 | Scheiner et al. | 2004/0034394 A1 | 2/2004 | Woods et al. |
| 6,600,956 | B2 | 7/2003 | Maschino | 2004/0054292 A1 | 3/2004 | Sun et al. |
| 6,611,713 | B2 | 8/2003 | Schaurte | 2004/0062852 A1 | 4/2004 | Schroeder et al. |
| 6,622,041 | B2 | 9/2003 | Terry et al. | 2004/0064172 A1 | 4/2004 | McVenes et al. |
| 6,666,826 | B2 | 12/2003 | Salo et al. | 2004/0102818 A1 | 5/2004 | Hakky et al. |
| 6,668,191 | B1 | 12/2003 | Boveja | 2004/0186523 A1 | 9/2004 | Florio |
| 6,669,645 | B2 | 12/2003 | Narimatsu et al. | 2004/0193231 A1 | 9/2004 | David et al. |
| 6,671,556 | B2 | 12/2003 | Osorio et al. | 2004/0199210 A1 | 10/2004 | Shelchuk |

| | | | |
|---|---|---|---|
| 2004/0210122 A1 | 10/2004 | Sieburg |
| 2004/0210271 A1 | 10/2004 | Campen et al. |
| 2004/0215263 A1 | 10/2004 | Virag et al. |
| 2004/0249416 A1 | 12/2004 | Yun et al. |
| 2004/0249417 A1 | 12/2004 | Ransbury et al. |
| 2004/0254616 A1 | 12/2004 | Rossing et al. |
| 2005/0010263 A1 | 1/2005 | Schaurte |
| 2005/0021092 A1 | 1/2005 | Yun et al. |
| 2005/0065553 A1 | 3/2005 | Ben-Ezra et al. |
| 2005/0143779 A1 | 6/2005 | Libbus |
| 2005/0143785 A1 | 6/2005 | Libbus |
| 2005/0149126 A1 | 7/2005 | Libbus |
| 2005/0149127 A1 | 7/2005 | Libbus |
| 2005/0149128 A1 | 7/2005 | Heil et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Scheiner et al. |
| 2005/0149156 A1 | 7/2005 | Libbus et al. |
| 2005/0154418 A1 | 7/2005 | Kieval et al. |
| 2005/0182468 A1 | 8/2005 | Hunter et al. |
| 2005/0197675 A1 | 9/2005 | David et al. |
| 2006/0004417 A1 | 1/2006 | Rossing et al. |
| 2006/0079945 A1 | 4/2006 | Libbus et al. |
| 2006/0089678 A1 | 4/2006 | Shalev |
| 2006/0100668 A1 | 5/2006 | Ben-David et al. |
| 2006/0111745 A1 | 5/2006 | Foreman et al. |
| 2006/0206155 A1 | 9/2006 | Ben-David et al. |
| 2006/0224222 A1 | 10/2006 | Bradely et al. |
| 2007/0021790 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0038278 A1 | 2/2007 | Zarembo |
| 2007/0049989 A1 | 3/2007 | Rossing et al. |
| 2007/0106340 A1 | 5/2007 | Bolea et al. |
| 2007/0161912 A1 | 7/2007 | Zhang et al. |
| 2007/0167984 A1 | 7/2007 | Kieval et al. |
| 2007/0179543 A1 | 8/2007 | Ben-David et al. |
| 2007/0185542 A1 | 8/2007 | Bolea et al. |
| 2007/0191895 A1 | 8/2007 | Foreman et al. |
| 2007/0191904 A1 | 8/2007 | Libbus et al. |
| 2008/0049376 A1 | 2/2008 | Stevenson et al. |
| 2008/0167694 A1 | 7/2008 | Bolea et al. |
| 2008/0171923 A1 | 7/2008 | Bolea et al. |
| 2008/0172101 A1 | 7/2008 | Bolea et al. |
| 2008/0177339 A1 | 7/2008 | Bolea et al. |
| 2008/0177348 A1 | 7/2008 | Bolea et al. |
| 2008/0177364 A1 | 7/2008 | Bolea et al. |
| 2008/0177365 A1 | 7/2008 | Bolea et al. |
| 2008/0177366 A1 | 7/2008 | Bolea et al. |

FOREIGN PATENT DOCUMENTS

| | | |
|---|---|---|
| WO | WO98/02209 | 1/1998 |
| WO | WO 99/26530 | 6/1999 |
| WO | WO 99/42039 | 8/1999 |
| WO | WO 99/42176 | 8/1999 |
| WO | WO99/51286 | 10/1999 |
| WO | WO00/16686 | 3/2000 |
| WO | WO 01/00273 | 1/2001 |
| WO | WO01/76469 | 10/2001 |
| WO | WO02/26314 | 4/2002 |
| WO | WO02/26318 | 4/2002 |
| WO | WO02/070039 | 9/2002 |
| WO | WO03/018107 | 3/2003 |
| WO | WO 03/076008 | 9/2003 |

OTHER PUBLICATIONS

"Baropacing of the Carotid Sinus Nerve for Treatment of Intractable Hypertension", Zeitschrift Fur Kardiologie, band 64, Heft 4, pp. 368-374, 1975.

"Baroreflex Anatomy", Human Baroreflexes in Health & Disease, pp. 19-30, 1992.

"Cardiovascular Reflexes From Ventricular & Coronary Receptors", Adv. Exp. Med. Biol., 1995, 381:157-74.

"Carotid Sinus Stimulation For the Treatment of Angina Pectoris", Official Journal of the Calif. Medical Assoc., vol. 112, No. 3, pp. 78-79, Mar. 1970.

"Circulatory Effects of Carotid Sinus Stimulation & Changes in Blood Volume Distribution in Hypertensive Man", Acta. Physiol. Scand., 1981, 111:299-306, Mar. 1981.

"Clinical Experience with a Helical Bipolar Stimulating Lead", PACE, vol. 15, Part II, Oct. 1992, pp. 1545-1556.

"Fine Structure of Baroreceptor Terminals in the Carotid Sinus of Guinea Pigs & Mice", Cell & Tissue Research, 170, pp. 95-112 , 1976.

"Implantation of a Carotid Sinus Nerve Stimulator", AORN Journal, pp. 53-56, Dec. 1969.

"Laryngospasm Induced by a Carotid-Sinus-Nerve Stimulator", The New England Journ. Of Med., No. 13, pp. 709-710, undated, admitted prior art.

"New Technique for Vagal Nerve Stimulation", Journal of Neuroscience Methods, 1999, pp. 109-114.

"Non-Invasive Heat-Delivery To Arterial Stented Segments In Vivo: Effect of Heat on Intimal Hyperplasia", JACC, 1041-89, Feb. 2000.

"Stimulation of the Carotid Baroreceptors Using a Radio-Frequency Method", Israel J. Med. Sci., vol. 1, No. 4, Jul. 1965, pp. 630-632.

"Structure of Rat Aortic Baroreceptors & Their Relationship to Connective Tissue", Journal of Neurocytology, pp. 401-414, 1979.

"Studies on the Carotid Body & the Carotid Sinus Effects on the Heart by Electrical Stimulation of the Carotid Sinus Wall", Jap. Heart J., vol. 13, No. 2, Mar. 1972, pp. 136-149.

"Surgical Treatment of Hypertension with Reference to Baropacing", The Amer. Jour. Of Cardiology, vol. 17, May 1966, pp. 663-667.

"The Haemodynamic Basis of Anginal Relief Produced By Stimulation of the Carotid Sinus Nerve", Acta Medica Academiae Scientiarum Hungaricae, 30 (1-2), pp. 61-65, 1973.

"The Treatment of Heart Disease", Heart Disease, Earl N. Silber, 2.sup.nd Edition, MacMillan Publishing Co., p. 1642, 1987.

Bilgutay, A.M., et al., "Baropacing, a New Concept in the Treatment of Hypertension", from Baroreceptors and Hypertension Proceedings of an International Symposium, Nov. 1965, p. 425-437.

Brattstrom, A., Influence of Continuous and Intermittent (R-Wave Triggered) Electrical Stimulation of the Carotid Sinus Nerve on the Static Characteristic of the Circularoty Regulator:, Experientia 28:414-416, 1972.

Correspondence, The New England of Journal of Medicine, vol. 281, Jul. 3, 1969, No. 2.

Peters et al., Cardiovascular response to time delays of electrocardiogram-coupled electrical stimulation of carotid sinus nerves in dogs, Journal of the Autonomic Nervous Systems, 25:173-180, 1988.

Peters et al., The Principle of Electrical Carotid Sinus Nerve Stimulation: A Nerve Pacemaker System for Angina Pectoris and Hypertension Therapy, Annals of Biomedical Engineering, 8:445-458, 1980.

Richter et al., The Course of Inhibition of Sympathetic Activity during Various Patterns of Carotid Sinus Nerve Stimulation, Pflugers Arch., 317:110-123, 1970.

Sedin, Responses of the Cardiovascular System to Carotid Sinus Nerve Stimulation, Upsala J Med Sci, 81:1-17, 1976.

Transvenous parasympathetic nerve stimulation in the inferior vena cava and atrioventricular conduction, J. Cardiovasc. Electrophysiol., Jan. 2000, 1 page.

U.S. Appl. No. 09/963,777, filed Sep. 26, 2001 entitled "Electrode Designs and Methods of Use for Cardiovascular Reflex Control Devices" to Robert S. Kieval et al.

Warzel et. al., Effects of carotis sinus nerve stimulation at different times in the respiratory and cardiac cycles on variability of heart rate and blood pressure of normotensive and renal hypertensive dogs, Journal of the Autonomic Nervous System, 26:121-127, 1989.

Warzel et. al., The Effect of Time of Electrical Stimulation of the Carotid Sinus on the Amount of Reduction in Arterial Pressure, Pflugers Arch., 337:39-44, 1972.

International Search Report for International Application No. PCT/US01/30249 dated Jan. 9, 2002.

European Search Report for European Application No. EP01975479 dated Aug. 29, 2005.

Partial European Search Report for EP09158665 dated Jul. 7, 2009.

Extended European Search Report for EP09158665 dated Sep. 29, 2009.

International Search Report for International Application No. PCT/US05/11501 dated Aug. 24, 2006.

Supplementary European Search Report for European Application EP05737549 dated Jan. 26, 2010.

International Search Report for International Application No. PCT/US03/09630 dated Sep. 24, 2003.

Supplementary European Search Report for European Application No. EP03716888 dated Nov. 4, 2009.

Office Action for JP 2003-579629 dated Sep. 8, 2008.

International Search Report for International Application No. PCT/US03/09764 dated Oct. 28, 2003.

Supplementary European Search Report for European Application No. EP03716913 dated Nov. 4, 2009.

International Search Report for International Application No. PCT/US06/61256 dated Jan. 2, 2008.

Braunwald et al., "Carotid Sinus Stimulation in the Treatment of Angina Pectoris and Supraventricular Tachycardia," Calif. Medicine., vol. 112, No. 3, pp. 41-50, Mar. 1970.

Chiou et al., "Selective Vagal Denervation of the Atria Eliminates Heart Rate Variability and Baroreflex Sensitivity While Preserving Ventricular Innervation," Circulation 1998, 98, pp. 380-368.

Coleridge et al., "Reflex Effects of Stimulating Baroreceptors in the Pulmonary Artery" J. Physiol. (1963), 166, pp. 197-210.

Coleridge et al., "Impulse in Slowly Conducting Vagal Fibers from Afferent Endings in the Veins Atria and Arteries of Dogs and Cats," Circ. Res., vol. 33, (Jul. 1973) pp. 87-97.

Dickinson, CJ, "Fainting Precipitated by Collapse-Firing of Venous Baroreceptors", The Lancet: vol. 342, Oct. 16, 1993, pp. 970-972.

Ebert et al., "Fentanyl-diazepam anesthesia with or without N20 does not attenuate cardiopulmonary baroreflex-mediated vasoconstrictor responses to controlled hypovolemia in humans," Anesth Analg (1988) vol. 67, No. 6, pp. 548-554.

Kostreva et al., "Hepatic Vein Hapatic Parenchrmal and Inferior Vena Caval Mechanoreceptors with Phrenic Afferents," Am. J. Physiol., vol. 265, 1993, pp. G15-G20.

Liguori et al., Arystole and Severe Bradycardia during Epidural Anesthesia in Orthopedic Patients, Anesthesiology: vol. 86(1), Jan. 1997, pp. 250-257.

McMahon et al., "Reflex responses from the main pulmonary artery and bifurcation in anesthetized dogs" Experimental Physiology, 2000 85, 4 pp. 411-419.

Mifflin et al. "Rapid Resetting of Low Pressure Vagal Receptors in the Superior Vena Cava of the Rat" Circ. Res vol. 51(1982) pp. 241-249.

Nishi et al. "Afferent Fibres From Pulmonary Arterial Baroreceptors in the Left Cardiac Sympathetic Nerve of the Cat," J. Physiol. 1974, 240, pp. 53-66.

Nusil, White Papers (abstract only), "Drug Delivery Market Summary," published Jun. 25, 2004, retrieved from the internet <<http://www.nusil.com/whitepapers/2004/index.aspx>>.

Rau et al., "Psychophysiology of Arterial Baroreceptors and the Etiology of Hypertension," Biol. Psychol., vol. 57 (2001) pp. 179-201.

Tsakiris, "Changes in Left Ventricular End Diastolic Volume Pressure Relationship After Acute Cardiac Denervation," Abstracts of the 40th Scientific Sessions, Supplement II to Circulation, vols. XXXV & XXXVI, Oct. 1967, II-253, 1 sheet.

Silverberg et al., "Treating Obstructive Sleep Apnea Improves Essential Hypertions and Quality of Life," American Family Physician, (2002) vol. 65, No. 2.

Shahar et al., "Sleep-disordered Breathing and Cardiovascular Disease: Cross-sectional Results of the Sleep Heart Health Study," American Journal of Respiratory and Critical Care Medicine, (2001), vol. 163.

Leung et al., "State of the Art: Sleep Apnea and Cardiovascular Disease," American Journal of Respiratory and Critical Care Medicine, (2001) vol. 164.

Bolter et al. "Influence of cervical sympathetic nerve stimulation on carotid sinus baroreceptor afferents," Experientia. 1980 Nov. 15;36(11):1301-1302.

Fan et al., "Graded and dynamic reflex summation of myelinated and unmyelinated rat aortic baroreceptors," Am J Physiol Regul Integr Comp Physiol, 1999 Sep;277(3):R748-756.

Image File Wrapper for U.S. Patent No. 6,522,926.
Image File Wrapper for U.S. Patent No. 6,985,774.
Image File Wrapper for U.S. Patent No. 7,158,832.
Image File Wrapper for U.S. Patent No. 6,850,801.
Image File Wrapper for U.S. Appl. No. 10/284,063.
Image File Wrapper for U.S. Publication No. 2008/0177365.
Image File Wrapper for U.S. Publication No. 2008/0177348.
Image File Wrapper for U.S. Publication No. 2008/0177366.
Image File Wrapper for U.S. Publication No. 2008/0167694.
Image File Wrapper for U.S. Publication No. 2008/0172101.
Image File Wrapper for U.S. Publication No. 2008/0171923.
Image File Wrapper for U.S. Publication No. 2008/0177364.
Image File Wrapper for U.S. Publication No. 2008/0177339.
Image File Wrapper for U.S. Publication No. 2008/0097540.
Image File Wrapper for U.S. Publication No. 2009/0228065.
Image File Wrapper for U.S. Appl. No. 12/731,104.
Image File Wrapper for U.S. Appl. No. 12/762,891.
Image File Wrapper for U.S. Appl. No. 12/785,287.
Image File Wrapper for U.S. Patent No. 7,616,997.
Image File Wrapper for U.S. Publication No. 2008/0167699.
Image File Wrapper for U.S. Publication No. 2009/0234418.
Image File Wrapper for U.S. Appl. No. 12/616,057.
Image File Wrapper for U.S. Appl. No. 12/719,696.
Image File Wrapper for U.S. Publication No. 2006/0111626.
Image File Wrapper for U.S. Publication No. 2009/0069738.
Image File Wrapper for U.S. Publication No. 2007/0038260.
Image File Wrapper for U.S. Publication No. 2007/0038261.
Image File Wrapper for U.S. Publication No. 2007/0038259.
Image File Wrapper for U.S. Publication No. 2007/0167984.
Image File Wrapper for U.S. Publication No. 2007/0060972.
Image File Wrapper for U.S. Publication No. 2008/0215111.
Image File Wrapper for U.S. Publication No. 2008/0177349.
Image File Wrapper for U.S. Publication No. 2008/0177350.
Image File Wrapper for U.S. Patent No. 7,499,742.
Image File Wrapper for U.S. Publication No. 2007/0021794.
Image File Wrapper for U.S. Publication No. 2007/0021797.
Image File Wrapper for U.S. Publication No. 2007/0038255.
Image File Wrapper for U.S. Publication No. 2007/0021798.
Image File Wrapper for U.S. Publication No. 2007/0038262.
Image File Wrapper for U.S. Publication No. 2007/0021799.
Image File Wrapper for U.S. Publication No. 2007/0021796.
Image File Wrapper for U.S. Publication No. 2007/0021790.
Image File Wrapper for U.S. Publication No. 2007/0106340.
Image File Wrapper for U.S. Publication No. 2007/0185542.
Image File Wrapper for U.S. Patent No. 7,623,926.
Image File Wrapper for U.S. Publication No. 2007/0049989.
Image File Wrapper for U.S. Publication No. 2007/0185543.
Image File Wrapper for U.S. Publication No. 2007/0021792.

* cited by examiner

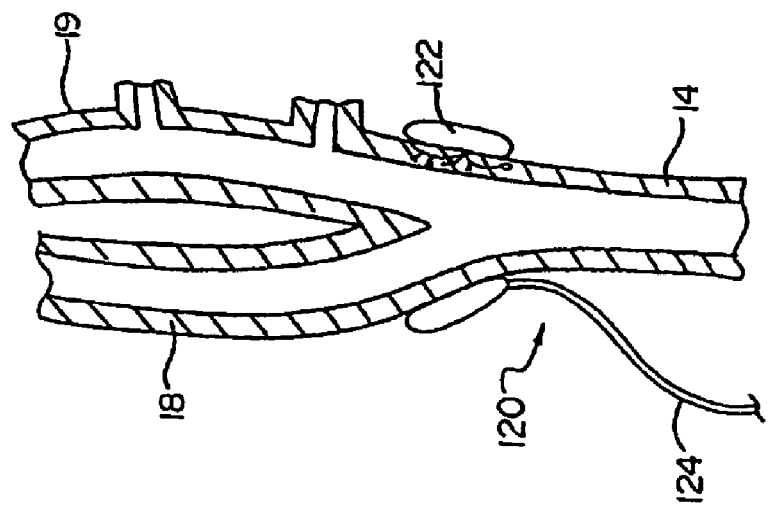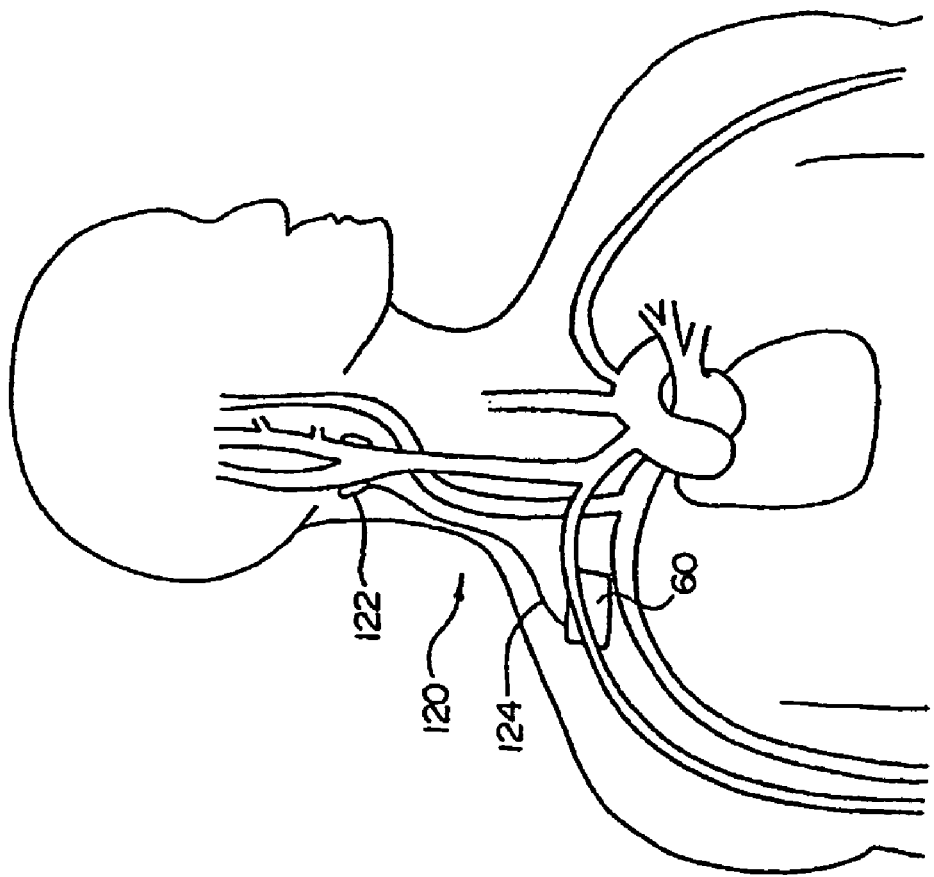

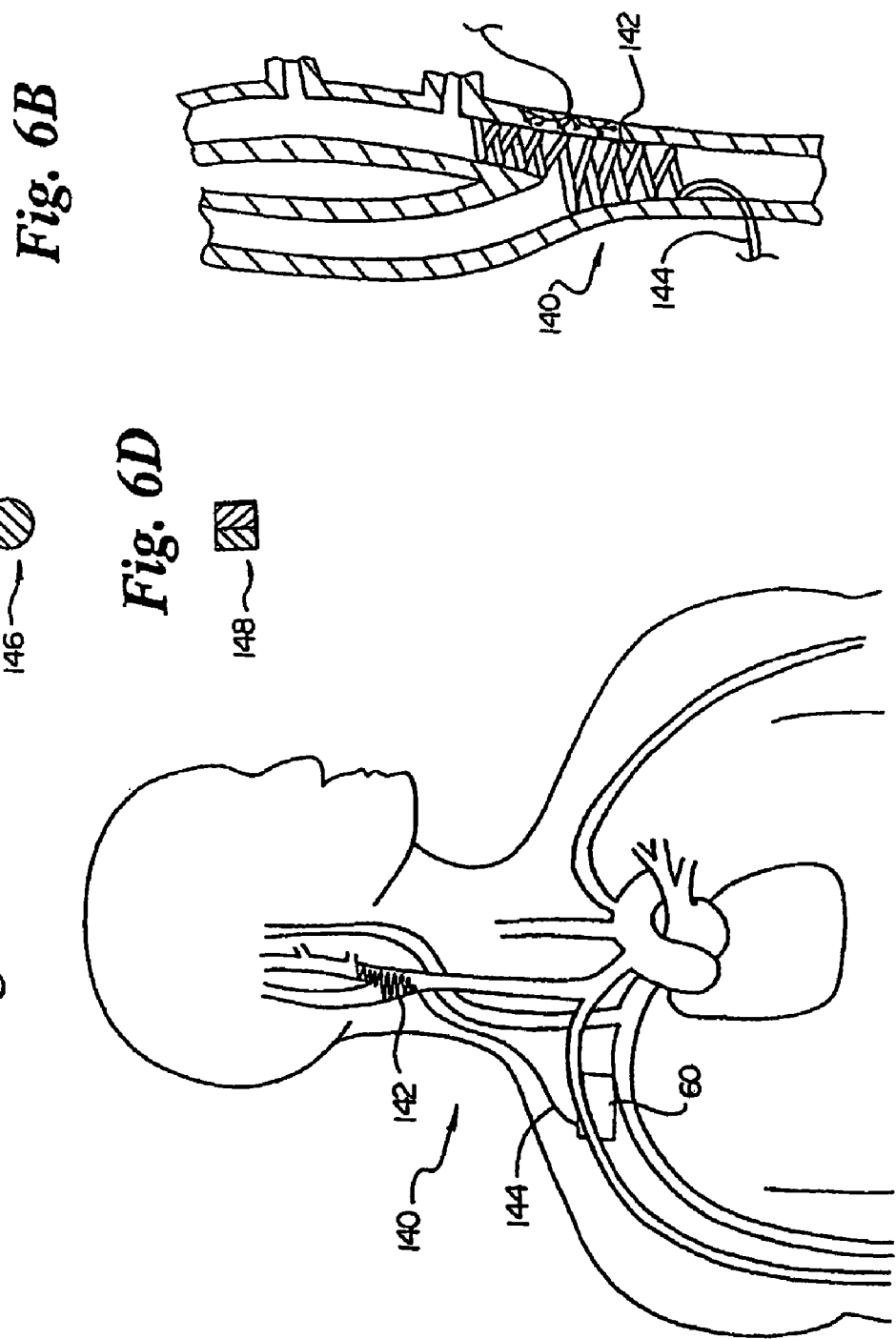

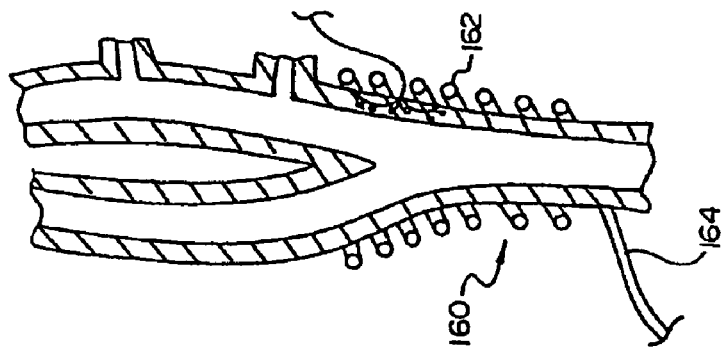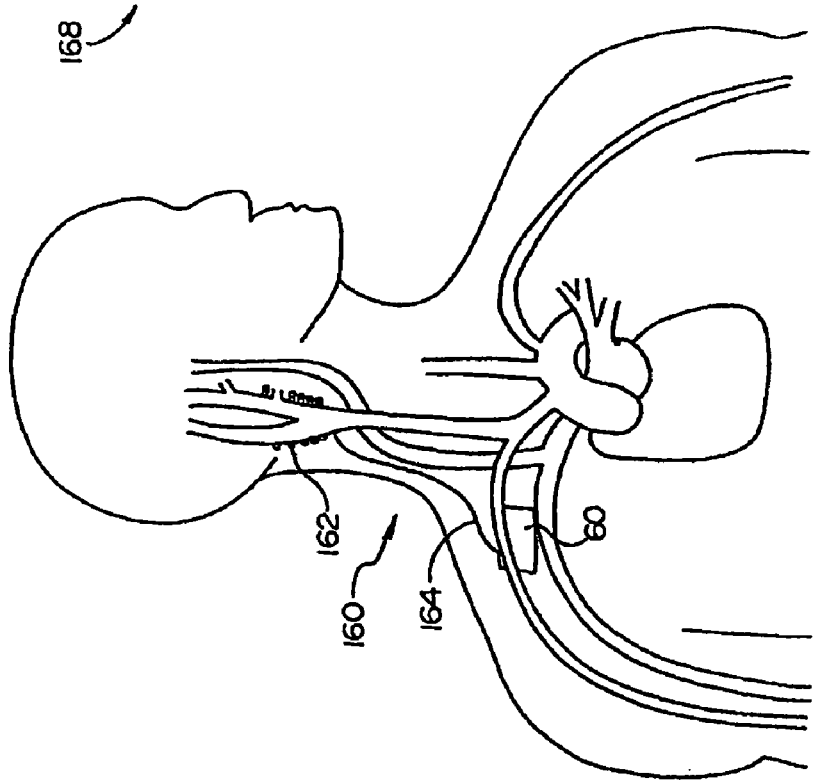

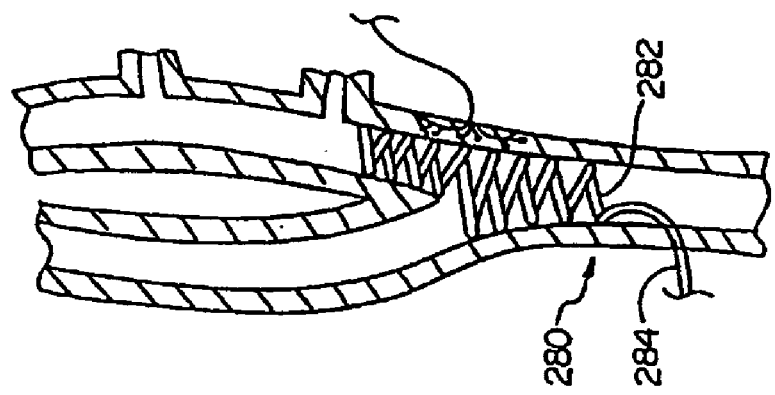
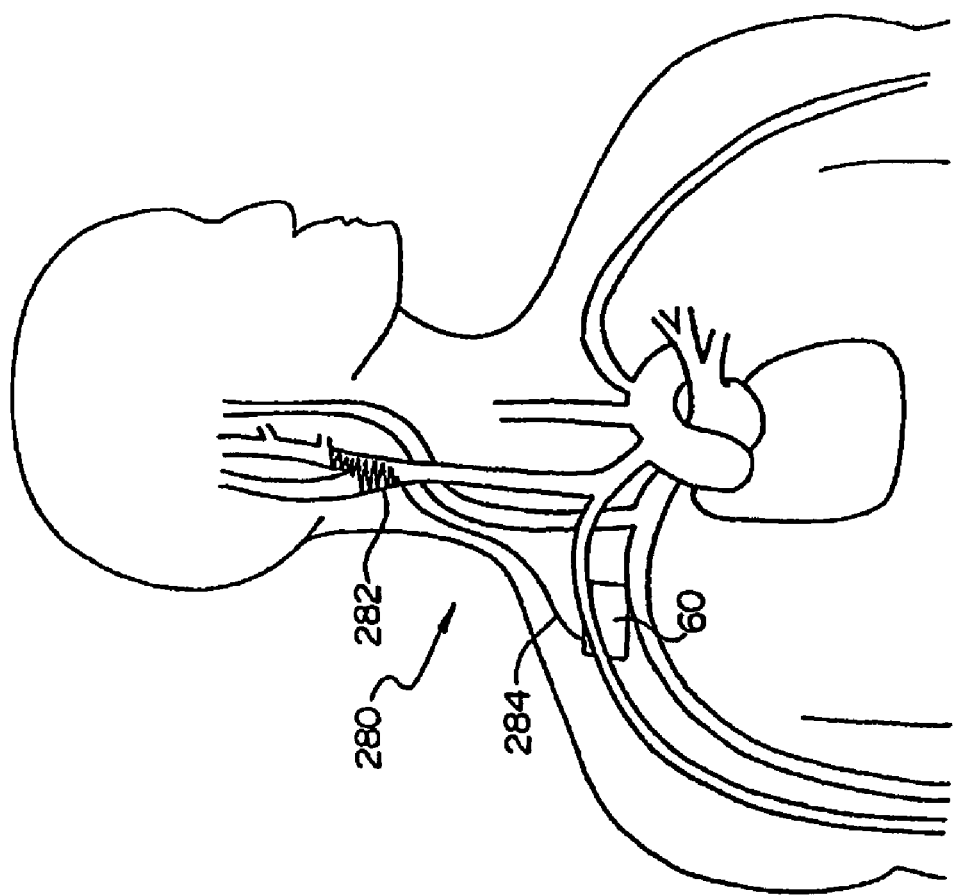

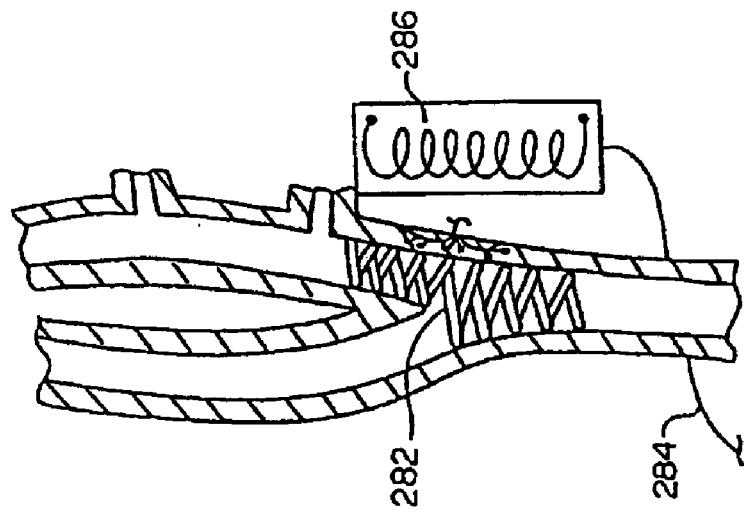
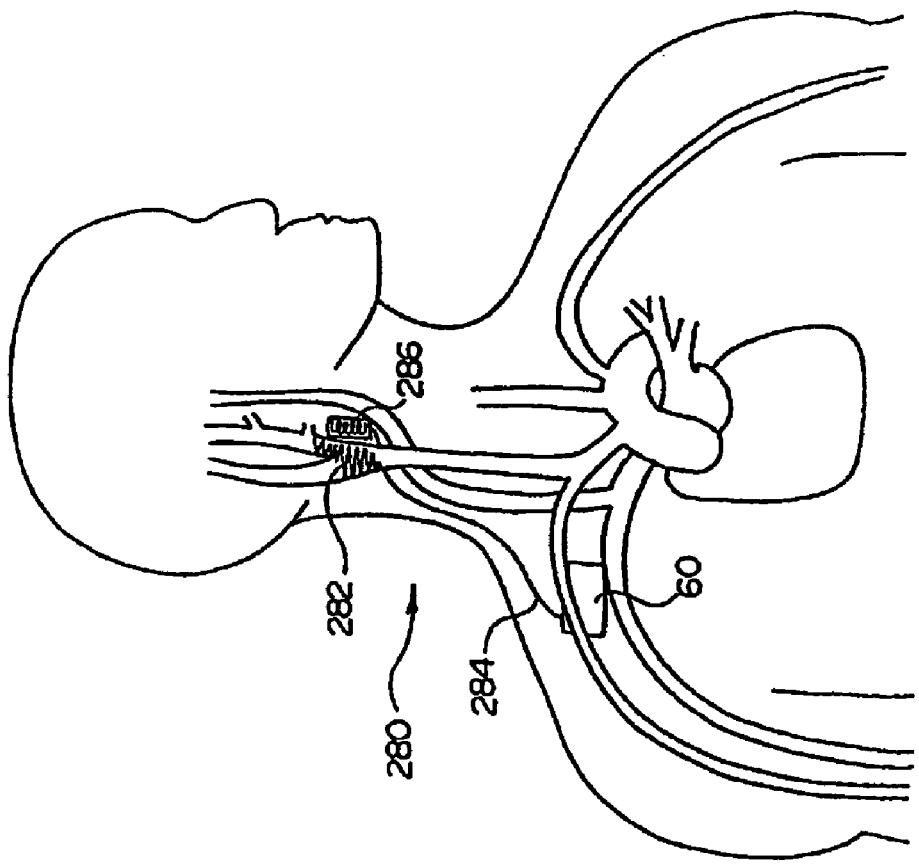

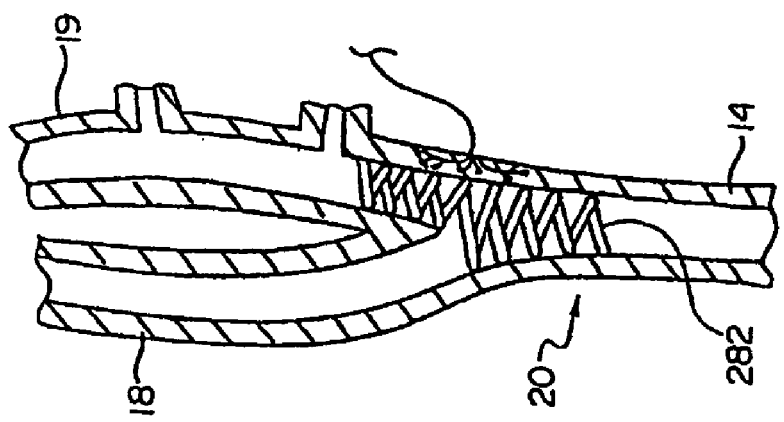
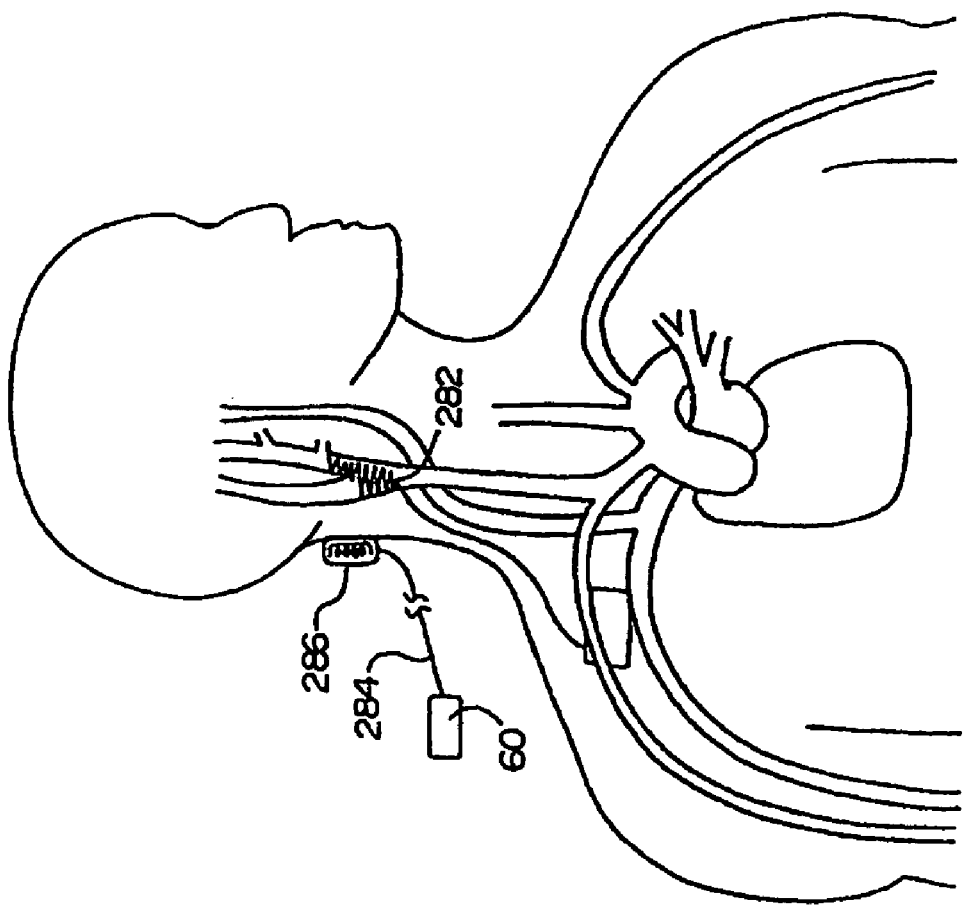

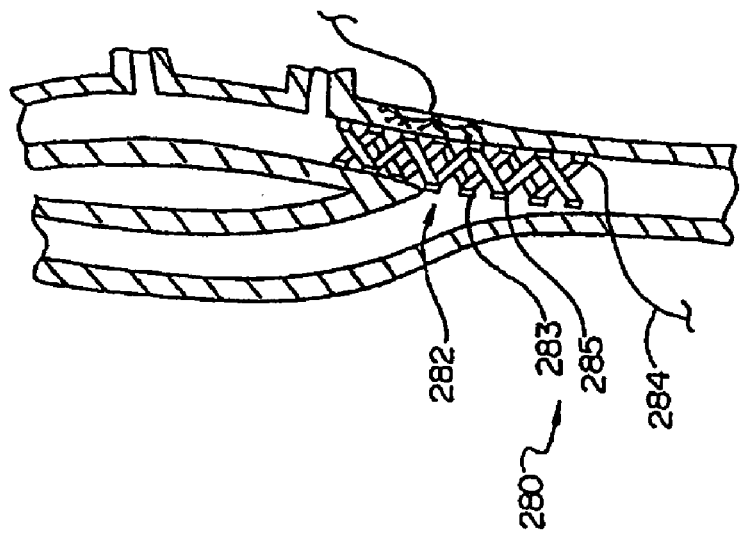
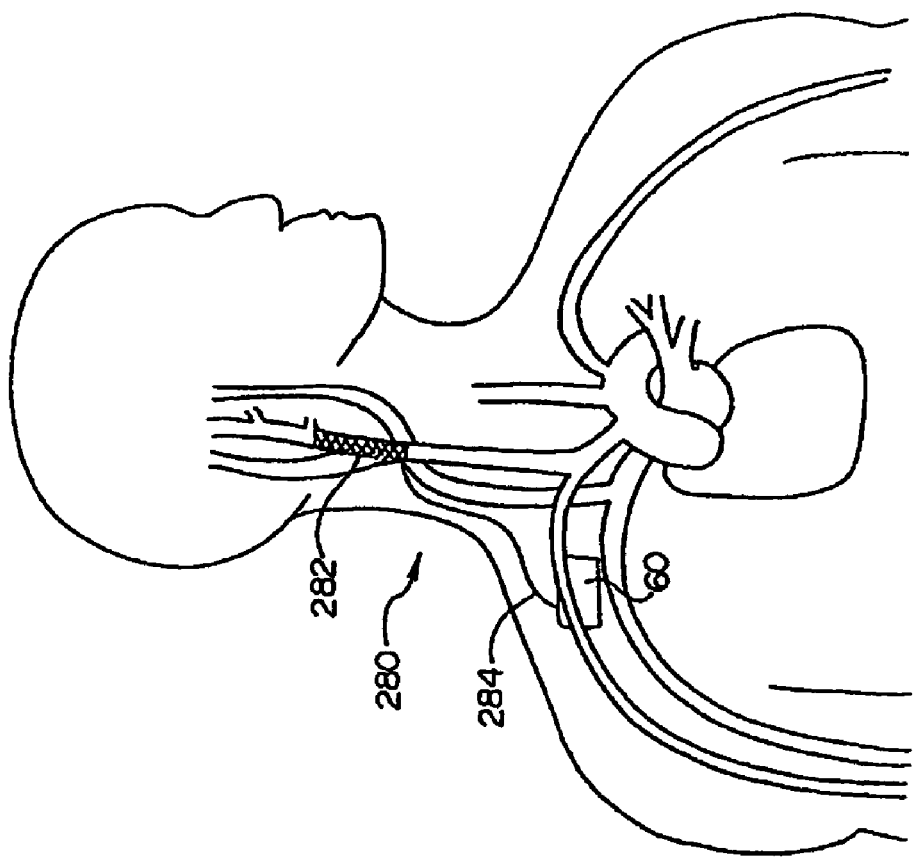

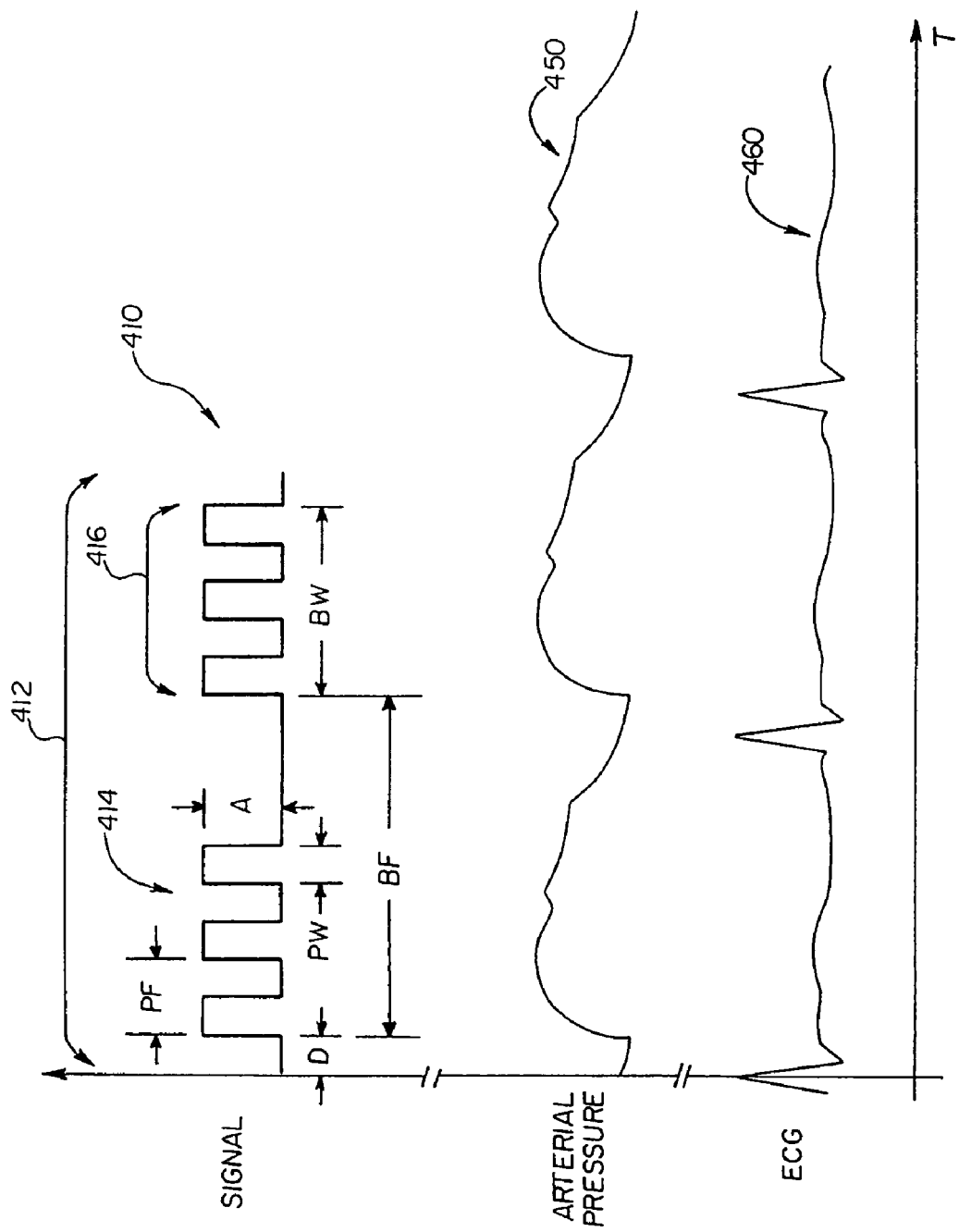

STIMULUS REGIMENS FOR CARDIOVASCULAR REFLEX CONTROL

CROSS-REFERENCES TO RELATED APPLICATIONS

This application is a divisional of application Ser. No. 09/964,079, now U.S. Pat. No. 6,985,774, filed on Sep. 26, 2001, which was a continuation-in-part of U.S. patent application Ser. No. 09/671,850, now U.S. Pat. No. 6,522,926, filed Sep. 27, 2000. This application is related to U.S. Pat. No. 7,158,832, filed on Sep. 26, 2001, and U.S. Pat. No. 6,850, 801, filed on Sep. 26, 2001. The entire disclosures of which are hereby incorporated by reference.

BACKGROUND OF THE INVENTION

1. Field of the Invention

The present invention generally relates to medical devices and methods of use for the treatment and/or management of cardiovascular and renal disorders. Specifically, the present invention relates to devices and methods for controlling the baroreflex system for the treatment and/or management of cardiovascular and renal disorders and their underlying causes and conditions.

2. Background of the Invention

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to effect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension may occur when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900, 000 hospital admissions annually, and is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Other surgical procedures are available as well.

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex arc based on various cardiovascular and pulmonary parameters.

Although each of these alternative approaches is beneficial in some ways, each of the therapies has its own disadvantages. For example, drug therapy is often incompletely effective. Some patients may be unresponsive (refractory) to medical therapy. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Baropacing also has not gained acceptance. Several problems with electrical carotid sinus nerve stimulation have been reported in the medical literature. These include the invasiveness of the surgical procedure to implant the nerve electrodes, and postoperative pain in the jaw, throat, face and head during stimulation. In addition, it has been noted that high voltages sometimes required for nerve stimulation may damage the carotid sinus nerves. Accordingly, there continues to be a substantial and long felt need for new devices and methods for treating and/or managing high blood pressure, heart failure and their associated cardiovascular and nervous system disorders.

Situations may also arise in which it would be beneficial to raise the blood pressure of a patient. For example, the patient may be experiencing a period of reduced blood pressure, or hypotension. Conditions associated with symptomatic hypotension include vasovagal reactions, orthostatic hypotension and dysautonomia. Alternatively, it may be advantageous to augment the blood pressure of a patient in whom the blood pressure may be normal or near normal, for example in claudication syndromes. Therefore, a also need exists for a therapy that can acutely increase the blood pressure in a patient.

BRIEF SUMMARY OF THE INVENTION

To address hypertension, heart failure and their associated cardiovascular and nervous system disorders, the present invention provides a number of devices, systems and methods by which the blood pressure, nervous system activity, and neurohormonal activity may be selectively and controllably regulated by activating baroreceptors. By selectively and controllably activating baroreceptors, the present invention reduces excessive blood pressure, sympathetic nervous system activation and neurohormonal activation, thereby minimizing their deleterious effects on the heart, vasculature and other organs and tissues. The present invention provides systems and methods for treating a patient by inducing a baroreceptor signal to effect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in the carotid sinus, aortic arch, heart, common carotid arteries, subclavian arteries, and/or brachiocephalic artery. Preferably, the baroreceptor activation device is located in the right and/or left carotid sinus (near the bifurcation of the common carotid artery) and/or the aortic arch. By way of example, not limitation, the present invention is described with reference to the carotid sinus location.

Generally speaking, the baroreceptor activation device may be activated, deactivated or otherwise modulated to activate one or more baroreceptors and induce a baroreceptor signal or a change in the baroreceptor signal to thereby effect a change in the baroreflex system. The baroreceptor activation device may be activated, deactivated, or otherwise modulated continuously, periodically, or episodically. The baroreceptor activation device may comprise a wide variety of devices which utilize mechanical, electrical, thermal, chemical, biological, or other means to activate the baroreceptor. The baroreceptor may be activated directly, or activated indirectly via the adjacent vascular tissue. The baroreceptor activation device may be positioned inside the vascular lumen (i.e., intravascularly), outside the vascular wall (i.e., extravascularly) or within the vascular wall (i.e., intramurally).

A control system may be used to generate a control signal which activates, deactivates or otherwise modulates the baroreceptor activation device. The control system may operate in an open-loop or a closed-loop mode. For example, in the open-loop mode, the patient and/or physician may directly or remotely interface with the control system to prescribe the control signal. In the closed-loop mode, the control signal may be responsive to feedback from a sensor, wherein the response is dictated by a preset or programmable algorithm defining a stimulus regimen.

The stimulus regimen is preferably selected to promote long term efficacy and to minimize requirements. It is theorized that uninterrupted activation of the baroreceptors may result in the baroreceptors and/or baroreflex system becoming less responsive over time, thereby diminishing the effectiveness of the therapy. Therefore, the stimulus regimen may be selected to modulate, for example, the baroreceptor activation device in such a way that the baroreceptors maintain their responsiveness over time. Specific examples of stimulus regimens which promote long term efficacy are described in more detail hereinafter.

BRIEF DESCRIPTION OF THE DRAWINGS

FIGS. 5A and 5B are schematic illustrations of a baroreceptor activation device in the form of an external pressure cuff which mechanically induces a baroreceptor signal in accordance with an embodiment of the present invention;

FIGS. 6A and 6B are schematic illustrations of a baroreceptor activation device in the form of an internal deformable coil structure which mechanically induces a baroreceptor signal in accordance with an embodiment of the present invention;

FIGS. 6C and 6D are cross-sectional views of alternative embodiments of the coil member illustrated in FIGS. 6A and 6B;

FIGS. 7A and 7B are schematic illustrations of a baroreceptor activation device in the form of an external deformable coil structure which mechanically induces a baroreceptor signal in accordance with an embodiment of the present invention;

FIGS. 7C and 7D are cross-sectional views of alternative embodiments of the coil member illustrated in FIGS. 7A and 7B;

FIGS. 13A and 13B are schematic illustrations of a baroreceptor activation device in the form of an internal conductive structure which electrically or thermally induces a baroreceptor signal in accordance with an embodiment of the present invention;

FIGS. 14A and 14B are schematic illustrations of a baroreceptor activation device in the form of an internal conductive structure, activated by an internal inductor, which electrically or thermally induces a baroreceptor signal in accordance with an embodiment of the present invention;

FIGS. 16A and 16B are schematic illustrations of a baroreceptor activation device in the form of an internal conductive structure, activated by an external inductor, which electrically or thermally induces a baroreceptor signal in accordance with an embodiment of the present invention;

FIGS. 18A and 18B are schematic illustrations of a baroreceptor activation device in the form of an internal bipolar conductive structure which electrically or thermally induces a baroreceptor signal in accordance with an embodiment of the present invention;

FIG. 22 illustrates an arterial pressure signal, an ECG signal and a control/output signal as a function of time;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
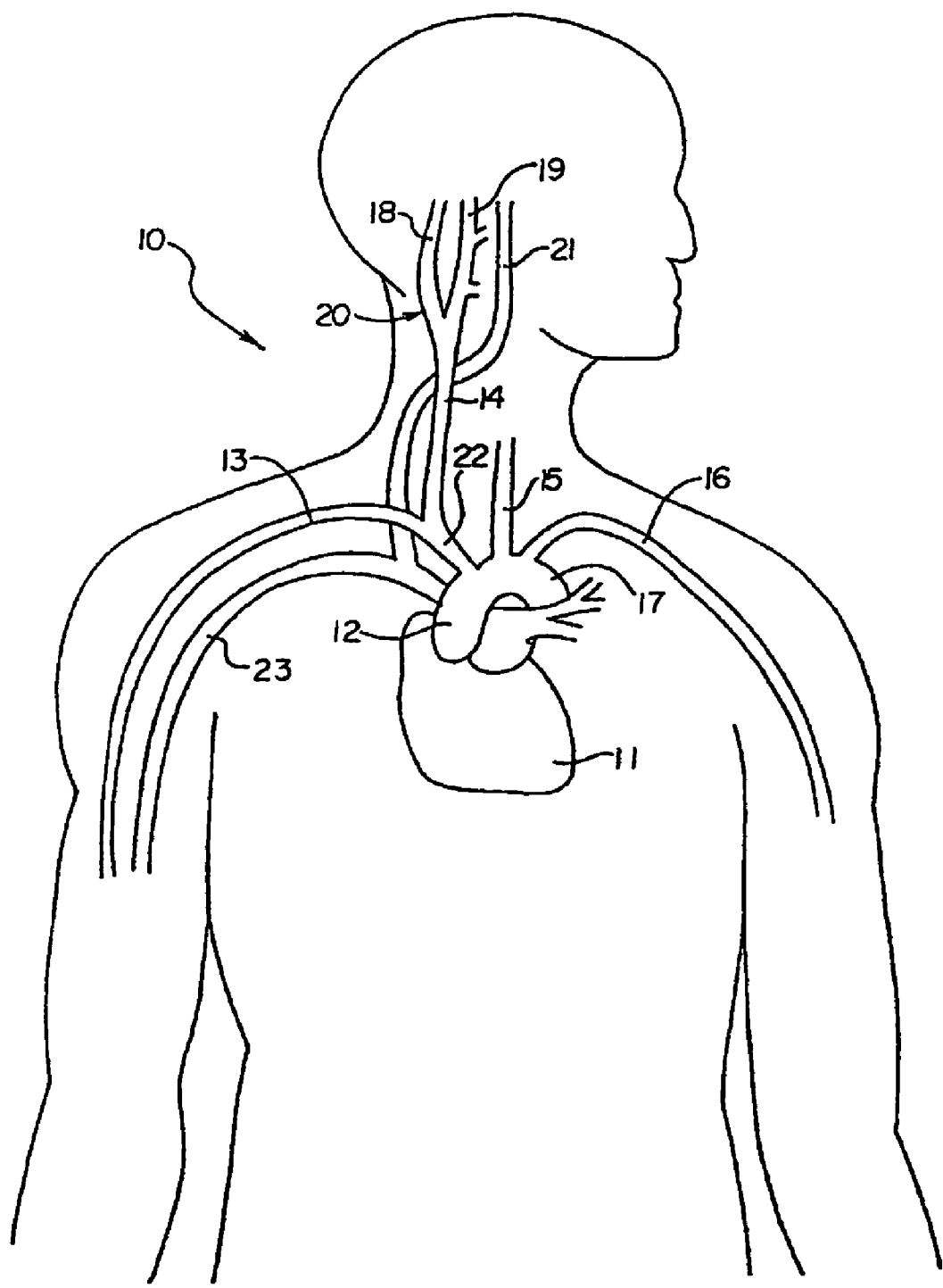
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. Because baroreceptors 30 are located within the arterial wall, they are able to sense deformation of the adjacent tissue, which is indicative of a change in blood pressure. The baroreceptors 30 located in the right carotid sinus 20, the left carotid sinus and the aortic arch 12 play the most significant role in sensing blood pressure that effects the baroreflex system 50, which is described in more detail with reference to FIG. 2B.

Figure 2B:
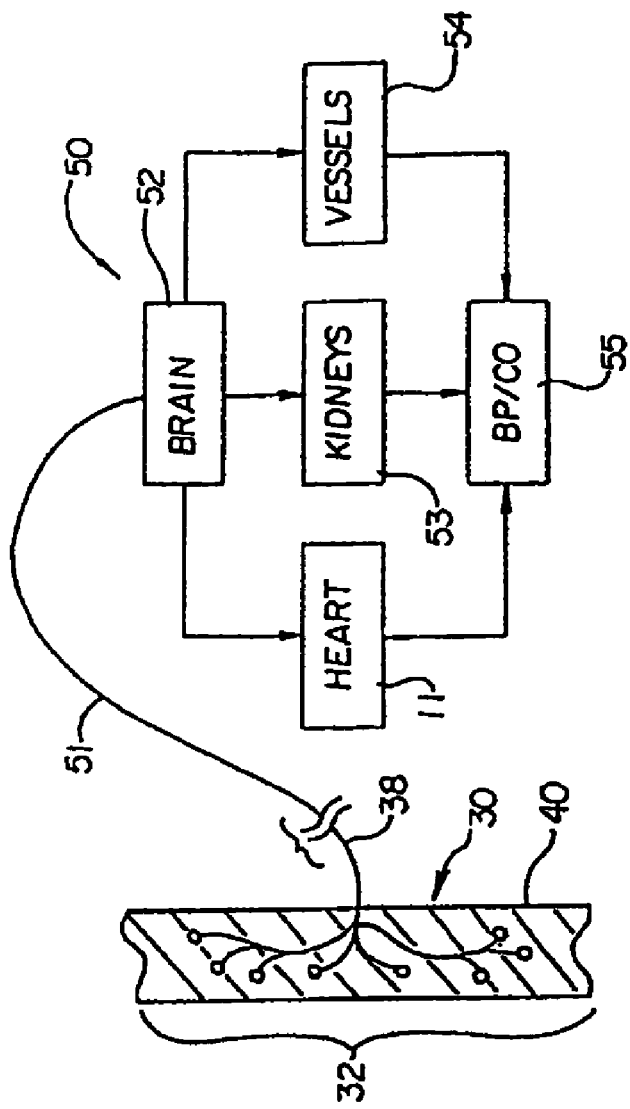
FIG. 2B is a schematic illustration of baroreceptors within the vascular wall and the baroreflex system.
Figure 2A:
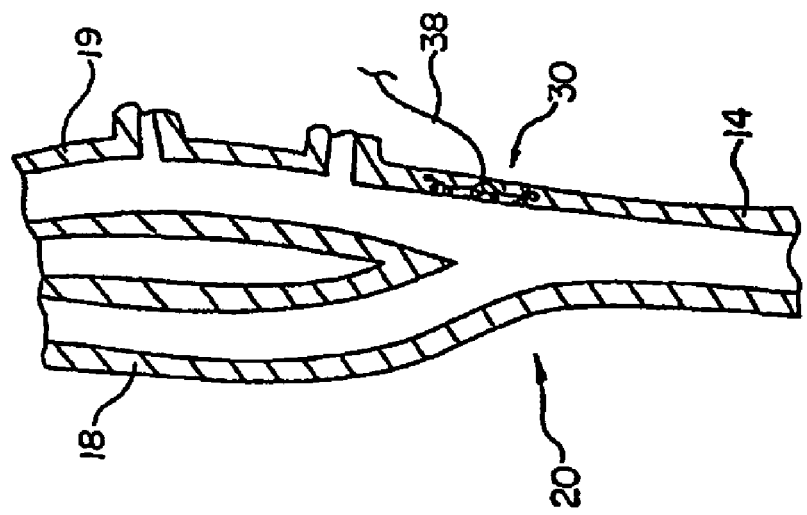
FIG. 2A is a cross-sectional schematic illustration of the carotid sinus and baroreceptors within the vascular wall.

Refer now to FIG. 2B, which shows a schematic illustration of baroreceptors 30 disposed in a generic vascular wall 40 and a schematic flow chart of the baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

Baroreceptor signals are used to activate a number of body systems which collectively may be referred to as the baroreflex system 50. Baroreceptors 30 are connected to the brain 52 via the nervous system 51. Thus, the brain 52 is able to detect changes in blood pressure, which is indicative of cardiac output. If cardiac output is insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state. To address the problems of hypertension, heart failure, other cardiovascular disorders and renal disorders, the present invention basically provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated, thereby indicating an increase in blood pressure and signaling the brain 52 to reduce the body's blood pressure and level of sympathetic nervous system and neurohormonal activation, and increase parasypathetic nervous system activation, thus having a beneficial effect on the cardiovascular system and other body systems.

Figure 3:
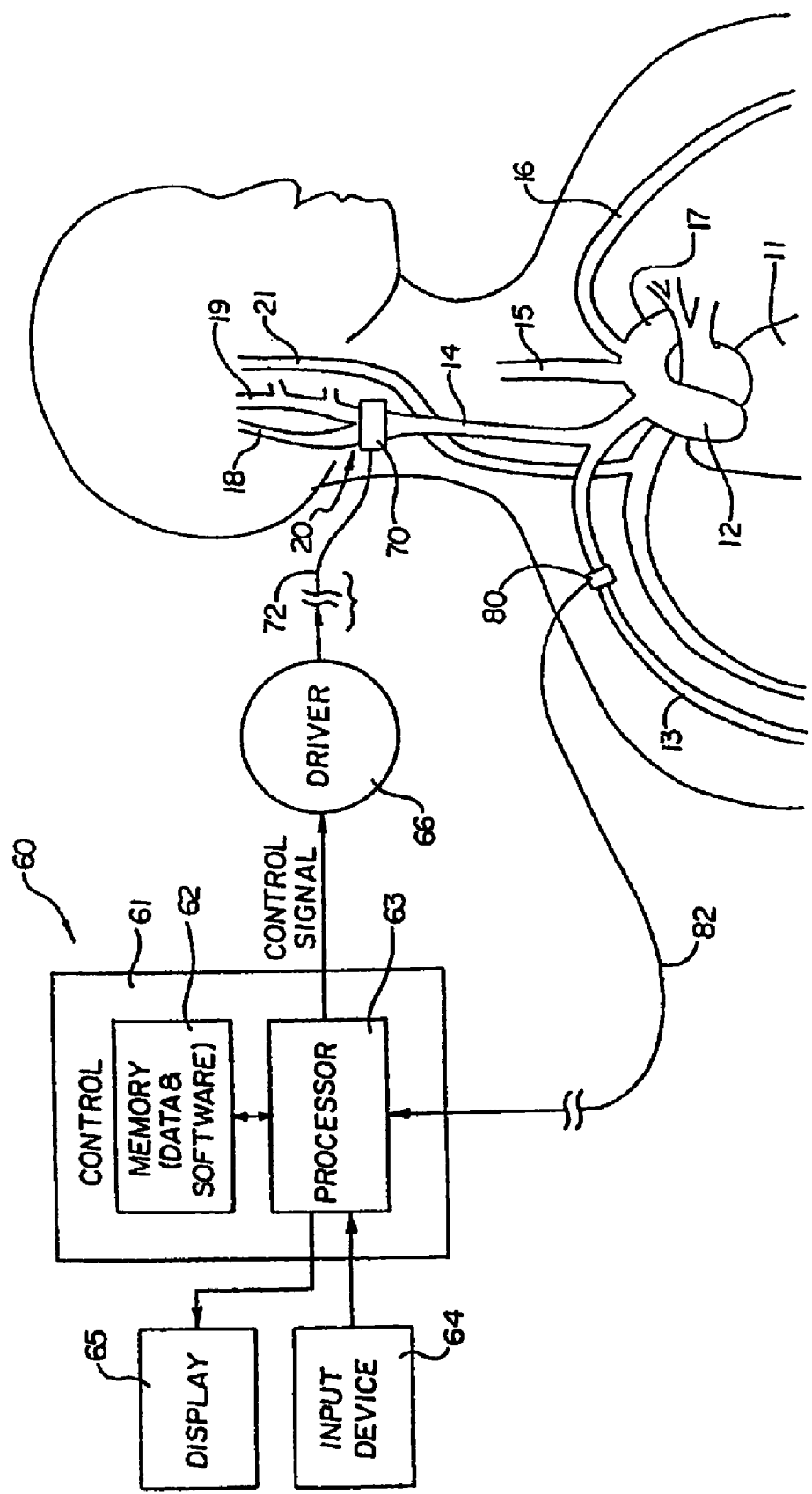
FIG. 3 is a schematic illustration of a baroreceptor activation system in accordance with the present invention.

With reference to FIG. 3, the present invention generally provides a system including a control system 60, a baroreceptor activation device 70, and a sensor 80 (optional), which generally operate in the following manner. The sensor 80 senses and/or monitors a parameter (e.g., cardiovascular function) indicative of the need to modify the baroreflex system and generates a signal indicative of the parameter. The control system 60 generates a control signal as a function of the received sensor signal. The control signal activates, deactivates or otherwise modulates the baroreceptor activation device 70. Typically, activation of the device 70 results in activation of the baroreceptors 30. Alternatively, deactivation or modulation of the baroreceptor activation device 70 may cause or modify activation of the baroreceptors 30. The baroreceptor activation device 70 may comprise a wide variety of devices which utilize mechanical, electrical, thermal, chemical, biological, or other means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreceptor activation device 70.

As mentioned previously, the baroreceptor activation device 70 may comprise a wide variety of devices which utilize mechanical, electrical, thermal, chemical, biological or other means to activate the baroreceptors 30. Specific embodiments of the generic baroreceptor activation device 70 are discussed with reference to FIGS. 4-21. In most instances, particularly the mechanical activation embodiments, the baroreceptor activation device 70 indirectly activates one or more baroreceptors 30 by stretching or otherwise deforming the vascular wall 40 surrounding the baroreceptors 30. In some other instances, particularly the non-mechanical activation embodiments, the baroreceptor activation device 70 may directly activate one or more baroreceptors 30 by changing the electrical, thermal or chemical environment or potential across the baroreceptors 30. It is also possible that changing the electrical, thermal or chemical potential across the tissue surrounding the baroreceptors 30 may cause the surrounding tissue to stretch or otherwise deform, thus mechanically activating the baroreceptors 30. In other instances, particularly the biological activation embodiments, a change in the function or sensitivity of the baroreceptors 30 may be induced by changing the biological activity in the baroreceptors 30 and altering their intracellular makeup and function. All of the specific embodiments of the baroreceptor activation device 70 are suitable for implantation, and are preferably implanted using a minimally invasive percutaneous translumenal approach and/or a minimally invasive surgical approach, depending on whether the device 70 is disposed intravascularly, extravascularly or within the vascular wall 40. The baroreceptor activation device 70 may be positioned anywhere baroreceptors 30 effecting the baroreflex system 50 are numerous, such as in the heart 11, in the aortic arch 12, in the common carotid arteries 18/19 near the carotid sinus 20, in the subclavian arteries 13/16, or in the brachiocephalic artery 22. The baroreceptor activation device 70 may be implanted such that the device 70 is positioned immediately adjacent the baroreceptors 30. Alternatively, the baroreceptor activation device 70 may be outside the body such that the device 70 is positioned a short distance from but proximate to the baroreceptors 30. Preferably, the baroreceptor activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreceptor activation device 70 positioned near the carotid sinus 20.

The optional sensor 80 is operably coupled to the control system 60 by electric sensor cable or lead 82. The sensor 80 may comprise any suitable device that measures or monitors a parameter indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, $O_2$ or $CO_2$ content, mixed venous oxygen saturation ($SVO_2$), vasoactivity, nerve activity, tissue activity or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector ($SVO_2$) or a strain gage. Although only one sensor 80 is shown, multiple sensors 80 of the same or different type at the same or different locations may be utilized.

The sensor 80 is preferably positioned in a chamber of the heart 11, or in/on a major artery such as the aortic arch 12, a common carotid artery 14/15, a subclavian artery 13/16 or the brachiocephalic artery 22, such that the parameter of interest may be readily ascertained. The sensor 80 may be disposed inside the body such as in or on an artery, a vein or a nerve (e.g., vagus nerve), or disposed outside the body, depending on the type of transducer or gauge utilized. The sensor 80 may be separate from the baroreceptor activation device 70 or combined therewith. For purposes of illustration only, the sensor 80 is shown positioned on the right subclavian artery 13.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

As mentioned previously, the baroreceptor activation device 70 may activate baroreceptors 30 mechanically, electrically, thermally, chemically, biologically or otherwise. In some instances, the control system 60 includes a driver 66 to provide the desired power mode for the baroreceptor activation device 70. For example if the baroreceptor activation device 70 utilizes pneumatic or hydraulic actuation, the driver 66 may comprise a pressure/vacuum source and the cable 72 may comprise fluid line(s). If the baroreceptor activation device 70 utilizes electrical or thermal actuation, the driver 66 may comprise a power amplifier or the like and the cable 72 may comprise electrical lead(s). If the baroreceptor activation device 70 utilizes chemical or biological actuation, the driver 66 may comprise a fluid reservoir and a pressure/vacuum source, and the cable 72 may comprise fluid line(s). In other instances, the driver 66 may not be necessary, particularly if the processor 63 generates a sufficiently strong electrical signal for low level electrical or thermal actuation of the baroreceptor activation device 70.

The control system 60 may operate as a closed loop utilizing feedback from the sensor 80, or as an open loop utilizing commands received by input device 64. The open loop operation of the control system 60 preferably utilizes some feedback from the transducer 80, but may also operate without feedback. Commands received by the input device 64 may directly influence the control signal or may alter the software and related algorithms contained in memory 62. The patient and/or treating physician may provide commands to input device 64. Display 65 may be used to view the sensor signal, control signal and/or the software/data contained in memory 62.

The control signal generated by the control system 60 may be continuous, periodic, episodic or a combination thereof, as dictated by an algorithm contained in memory 62. The algorithm contained in memory 62 defines a stimulus regimen which dictates the characteristics of the control signal as a function of time, and thus dictates the stimulation of baroreceptors as a function of time. Continuous control signals include a pulse, a train of pulses, a triggered pulse and a triggered train of pulses, all of which are generated continuously. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, etc.).

The stimulus regimen governed by the control system 60 may be selected to promote long term efficacy. It is theorized that uninterrupted or otherwise unchanging activation of the baroreceptors 30 may result in the baroreceptors and/or the baroreflex system becoming less responsive over time, thereby diminishing the long-term effectiveness of the therapy. Therefore, the stimulus regimen may be selected to activate, deactivate or otherwise modulate the baroreceptor activation device 70 in such a way that therapeutic efficacy is maintained long term.

In addition to maintaining therapeutic efficacy over time, the stimulus regimens of the present invention may be selected reduce power requirement/consumption of the system 60. As will be described in more detail hereinafter, the stimulus regimen may dictate that the baroreceptor activation device 70 be initially activated at a relatively higher energy and/or power level, and subsequently activated at a relatively lower energy and/or power level. The first level attains the desired initial therapeutic effect, and the second (lower) level sustains the desired therapeutic effect long term. By reducing the energy and/or power level after the desired therapeutic effect is initially attained, the power required or consumed by the activation device 70 is also reduced long term. This may correlate into systems having greater longevity and/or reduced size (due to reductions in the size of the power supply and associated components).

Another advantage of the stimulus regimens of the present invention is the reduction of unwanted collateral tissue stimulation. As mentioned above, the stimulus regimen may dictate that the baroreceptor activation device 70 be initially activated at a relatively higher energy and/or power level to attain the desired effect, and subsequently activated at a relatively lower energy and/or power level to maintain the desired effect. By reducing the output energy and/or power level, the stimulus may not travel as far from the target site, thereby reducing the likelihood of inadvertently stimulating adjacent tissues such as muscles in the neck and head.

Such stimulus regimens may be applied to all baroreceptor activation embodiments described herein. In addition to baroreceptor activation devices 70, such stimulus regimens may be applied to the stimulation of the carotid sinus nerves or other nerves effecting the baroreflex system. In particular, the stimulus regimens described herein may be applied to baropacing (i.e., electrical stimulation of the carotid sinus nerve), which has been proposed to reduce blood pressure and the workload of the heart in the treatment of high blood pressure and angina. For example, the stimulus regimens of the present invention may be applied to the baropacing system disclosed in U.S. Pat. No. 6,073,048 to Kieval et al., the entire disclosure of which is incorporated herein by reference.

The stimulus regimen may be described in terms of the control signal and/or the output signal from the baroreceptor activation device 70. Generally speaking, changes in the control signal result in corresponding changes in the output of the baroreceptor activation device 70 which effect corresponding changes in the baroreceptors 30. The correlation between changes in the control signal and changes in the baroreceptor activation device 70 may be proportional or disproportional, direct or indirect (inverse), or any other known or predictable mathematical relationship. For purposes of illustration only, the stimulus regimen may be described herein in such a way that assumes the output of the baroreceptor activation device 70 is directly proportional to the control signal.

A first general approach for a stimulus regimen which promotes long term efficacy and reduces power requirements/consumption involves generating a control signal to cause the baroreceptor activation device 70 to have a first output level of relatively higher energy and/or power, and subsequently changing the control signal to cause the baroreceptor activation device 70 to have a second output level of relatively lower energy and/or power. The first output level may be selected and maintained for sufficient time to attain the desired initial effect (e.g., reduced heart rate and/or blood pressure), after which the output level may be reduced to the second level for sufficient time to sustain the desired effect for the desired period of time.

For example, if the first output level has a power and/or energy value of X1, the second output level may have a power and/or energy value of X2, wherein X2 is less than X1. In some instances, X2 may be equal to zero, such that the first level is "on" and the second level is "off". It is recognized that power and energy refer to two different parameters, but may, at least in some contexts, be used interchangeably. Generally speaking, power is a time derivative of energy. Thus, in some cases, a change in one of the parameters (power or energy) may not correlate to the same or similar change in the other parameter. In the present invention, it is contemplated that a change in one or both of the parameters may be suitable to obtain the desired result of promoting long term efficacy.

It is also contemplated that more than two levels may be used. Each further level may increase the output energy or power to attain the desired effect, or decrease the output energy or power to retain the desired effect. For example, in some instances, it may be desirable to have further reductions in the output level if the desired effect may be sustained at lower power or energy levels. In other instances, particularly when the desired effect is diminishing or is otherwise not sustained, it may be desirable to increase the output level until the desired effect is reestablished, and subsequently decrease the output level to sustain the effect.

The transition from each level may be a step function (e.g., a single step or a series of steps), a gradual transition over a period of time, or a combination thereof. In addition, the signal levels may be continuous, periodic or episodic as discussed previously.

The output (power or energy) level of the baroreceptor activation device 70 may be changed in a number of different ways depending on the mode of activation utilized. For example, in the mechanical activation embodiments described herein, the output level of the baroreceptor activation device 70 may be changed by changing the output force/pressure, tissue displacement distance, and/or rate of tissue displacement. In the thermal activation embodiments described herein, the output level of the baroreceptor activation device 70 may be changed by changing the temperature, the rate of temperature increase, or the rate of temperature decrease (dissipation rate). In the chemical and biological activation embodiments described herein, the output level of the baroreceptor activation device 70 may be changed by changing the volume/concentration of the delivered dose and/or the dose delivery rate.

In electrical activation embodiments using a non-modulated signal, the output (power or energy) level of the baroreceptor activation device 70 may be changed by changing the voltage, current and/or signal duration. The output signal of the baroreceptor activation device 70 may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics include, but are not limited to: pulse amplitude (PA), pulse frequency (PF), pulse width or duration (PW), pulse waveform (square, triangular, sinusoidal, etc.), pulse polarity (for bipolar electrodes) and pulse phase (monophasic, biphasic).

In electrical activation embodiments wherein the output signal comprises a pulse train, several other signal characteristics may be changed in addition to the pulse characteristics described above. As illustrated in FIG. 22, the control or output signal 410 may comprise a pulse train 412 which generally includes a series of pulses 414 occurring in bursts 416. Pulse train 412 characteristics which may be changed include, but are not limited to: burst amplitude (equal to pulse amplitude if constant within burst packet 416), burst waveform (i.e., pulse amplitude variation within burst packet 416), burst frequency (BF), and burst width or duration (BW). The signal 410 or a portion thereof (e.g., burst 416 within the pulse train 412) may be triggered by any of the events discussed previously, or by a particular portion of the arterial pressure signal 450 or the ECG signal 460 (e.g., R-wave as shown in FIG. 22), or another physiologic timing indicator. If the signal 410 or a portion thereof is triggered, the triggering event may be changed and/or the delay from the triggering event may be changed.

A second general approach for a stimulus regimen which promotes long term efficacy and reduces power requirements/consumption involves the use of one baroreceptor activation device 70 having multiple output means (e.g., electrodes) or the use of multiple baroreceptor activation devices 70 each having a single or multiple output means. Basically, the stimulus regimen according to this approach calls for alternating activation of two or more devices 70 or output means, which are positioned at different anatomical locations. Alternating activation may be accomplished by alternating the control signal between the devices or output means. As used in this context, switching or alternating activation includes switching between individual output means, switching between sets of output means and individual output means, and switching between different sets of output means. By alternating activation between two or more different anatomical locations, the exposure of any single anatomical location to an output signal is reduced.

More specifically, a first device 70 or output means may be connected to a first baroreceptor location, and a second device 70 or output means may be connected to a second baroreceptor location, wherein the first location is different from the second location, and the control signal alternates activation of the first and second devices or output means. Although described with reference to two (first and second) devices 70 or output means, more than two may be utilized. By way of example, not limitation, a first device 70 or output means may be connected to the right carotid sinus, and a second device 70 or output means may be connected to the left carotid sinus. Alternatively, a first device 70 or output means may be connected to the left internal carotid artery, and a second device 70 or output means may be connected to the right internal carotid artery. As yet another alternative, first and second devices 70 or output means may be disposed next to each other but separated by a small distance (e.g., electrodes with multiple contact points). In each instance, the control signal alternates activation of the first and second devices or output means to reduce the signal exposure for each anatomical location. Those skilled in the relevant art will recognize that there are many possible anatomical combinations within the scope of this approach which are not specifically mentioned herein for sake of simplicity only. A third general approach for a stimulus regimen which promotes long term efficacy and reduces power requirements/consumption involves changing the time domain characteristics and/or the triggering event characteristics of the therapy. For example, a periodic control signal which has a designated start time (e.g., beginning of each minute, hour or day; specific time of day) and a designated duration (e.g., 1 second, 1 minute, 1 hour) may have a change in the designated start time and/or duration. Alternatively, an episodic control signal which is triggered by an episode (e.g., activation by the patient/physician, a particular part of the ECG signal, an increase in blood pressure above a certain threshold, specific time of day, etc.) may have a change in the delay from the triggering event or a change in the triggering event itself. For this latter alternative, the triggering event may be provided by feedback control utilizing sensor 80. As a further alternative, the control signal may be asynchronous, wherein the start time, duration or delay from a base line event is asynchronous (e.g., random).

Any of the foregoing approaches may be utilized alone or in combination. The use of a combination of approaches may further promote long term efficacy and may further reduce power requirements/consumption.

Figure 23:
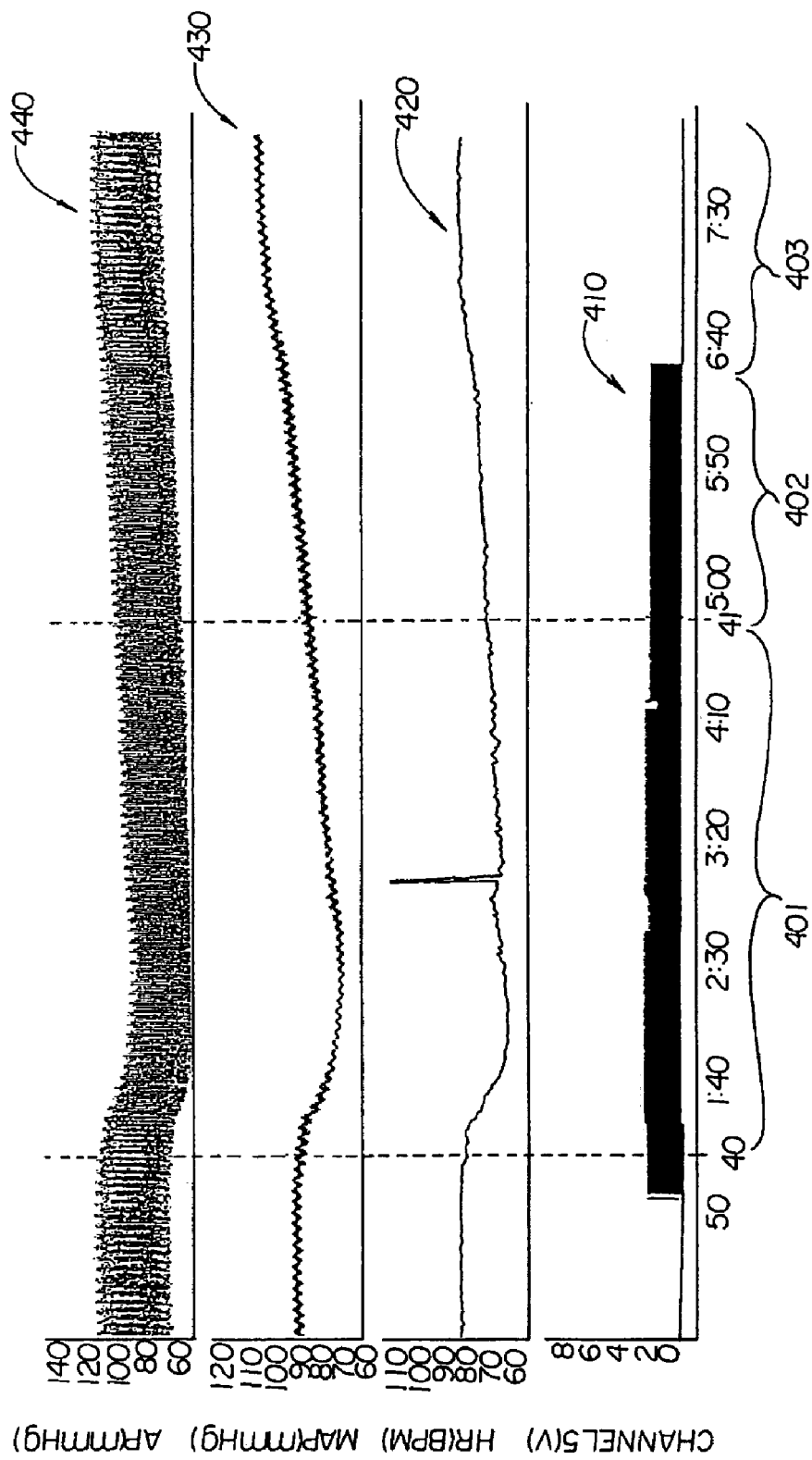
FIGS. 23-25 are graphs which illustrate the effectiveness of various stimulus regimens in accordance with various embodiments of the present invention.

To demonstrate the effectiveness of the first approach described above, an animal experiment was performed utilizing a baroreceptor activation device 70 in the form of an extravascular electrical activation device bilaterally (right and left) applied to the carotid sinus 20. The results of this experiment are illustrated in FIG. 23, which shows the control signal (volts) 410, heart rate (beats per minute) 420, mean arterial pressure (mmHg) 430 and arterial pressure (mmHg) 440 plotted as a function of time. The control signal 410 comprised a pulse train having a pulse amplitude of 2.5 volts, an initial pulse width or duration of 1.0 millisecond, and a pulse frequency of 100 Hz applied for a first period 401 of approximately 4 minutes. During this first period 401, the blood pressure 430/440 and heart rate 420 were significantly reduced. Subsequently, the pulse duration was changed to a 0.25 milliseconds and applied for a second period 402 of approximately 2 minutes, while the other parameters remained unchanged. During this second period 402, the reduced blood pressure 430/440 and heart rate 420 were sustained. After the second period 402, the pulse train was turned off for a period of time 403. During this third period 403, the blood pressure 430/440 and heart rate 420 began to gradually rise to their pretest values. This stimulus regimen demonstrated that the desired therapeutic effect may be sustained after reducing the pulse width of the stimulus device.

Figure 24:
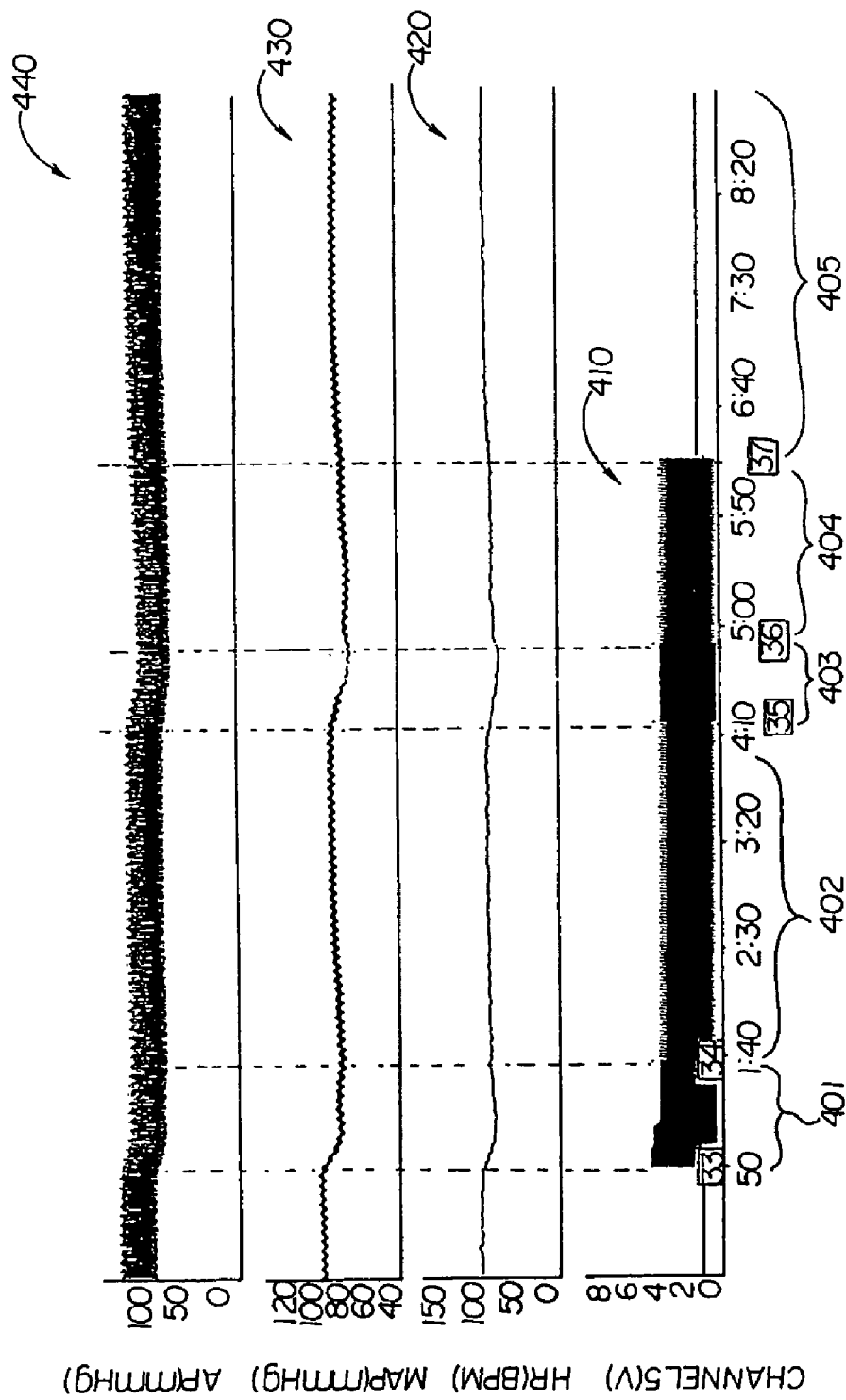

Another demonstration of the effectiveness of the first approach, is illustrated in FIG. 24, which shows the results of an animal experiment utilizing a baroreceptor activation device 70 in the form of an extravascular electrical activation device bilaterally (right and left) applied to the carotid sinus 20. FIG. 24 shows the control/output signal (volts) 410, heart rate (beats per minute) 420, mean arterial pressure (mmHg) 430 and arterial blood pressure (mmHg) 440 plotted as a function of time. The control signal 410 comprised a pulse train having a pulse amplitude of 2.5 volts, a pulse duration of 1.0 millisecond, and an initial pulse frequency of 100 Hz applied for a first period 401 of approximately 1 minute. During this first period 401, the heart rate 420 and blood pressure 430/440 were significantly reduced. The control signal 410 was changed to a pulse frequency of 10 Hz, while the pulse amplitude and duration remained unchanged, for a second period 402 of approximately 4 minutes. During this second period 402, the reduced heart rate and blood pressure were substantially sustained. The control signal 410 was changed back to a pulse frequency of 100 Hz, while the pulse amplitude and duration remained unchanged, for a third period 403 of approximately 40 seconds. During this third period 403, the heart rate 420 and blood pressure 430/440 were further reduced. The control signal 410 was changed again to a pulse frequency of 10 Hz, while the pulse amplitude and duration remained unchanged, for a fourth period 404 of approximately 1.5 minutes. During this fourth period 404, the reduced heart rate 420 and blood pressure 430/440 were substantially sustained. After the fourth period 404, the pulse train was turned off for a fifth period of time 405. During this fifth third period 405, the blood pressure 430/440 and heart rate 420 began to gradually rise to their pretest values.

Figure 25:
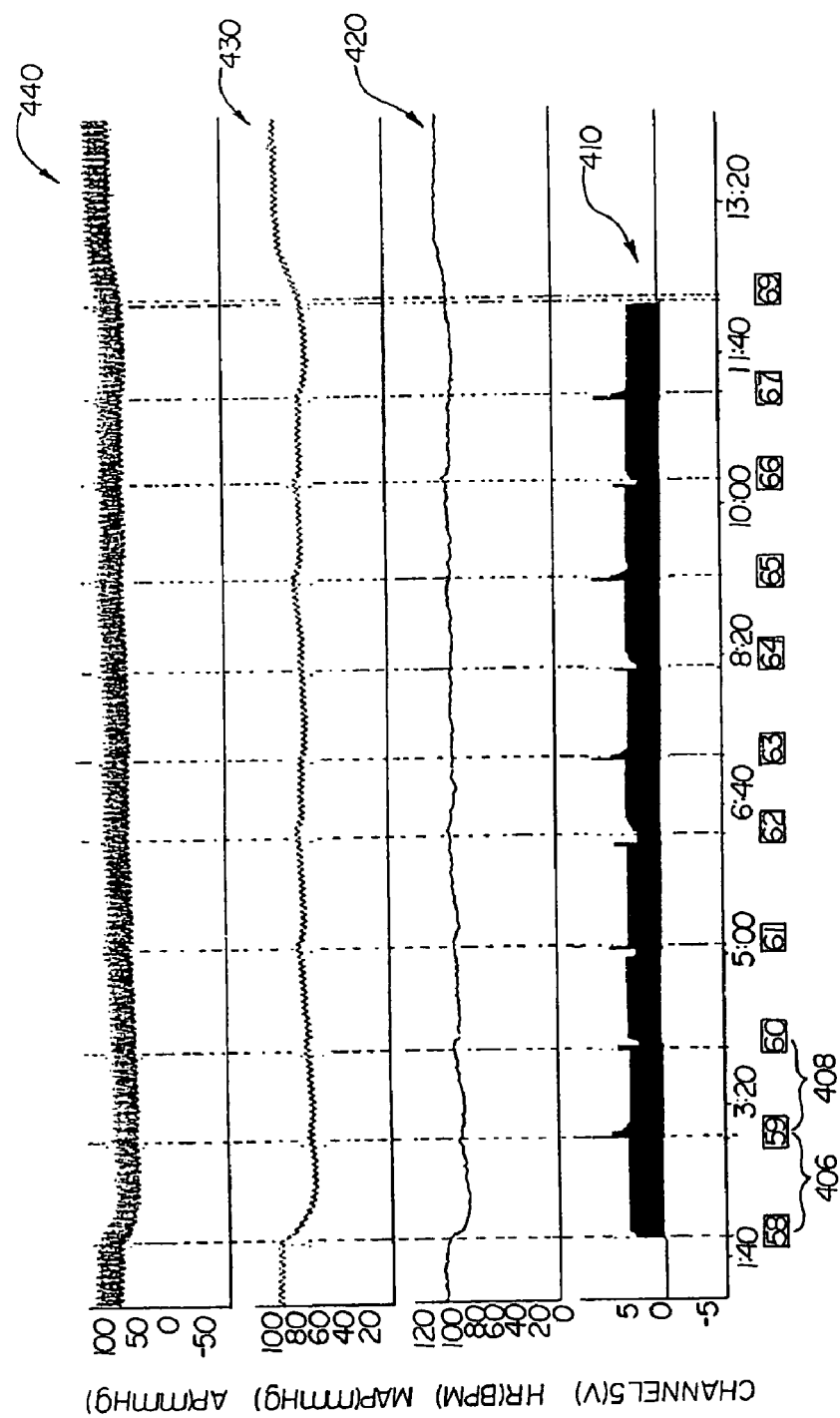

A demonstration of effectiveness of the second approach is illustrated in FIG. 25, which shows the results of an animal experiment wherein a baroreceptor activation device 70 in the form of an extravascular activation device having two electrodes was utilized. A first electrode was connected to the right carotid sinus and a second electrode was connected to the left carotid sinus. FIG. 25 shows the control signal (volts) 410, heart rate (beats per minute) 420, mean arterial pressure (mmHg) 430 and arterial blood pressure (mmHg) 440 plotted as a function of time. The control/output signal 410 comprised a pulse train having a pulse amplitude of 4.0 volts, a pulse duration of 1.0 millisecond, and a pulse frequency of 100 Hz applied for a 60 second period 406 to the left side. During this period 406, the heart rate 420 and blood pressure 430/440 were significantly reduced. The control signal 410 was switched to the right side for a 60 second period 408, while sustaining the reduced heart rate and blood pressure. The control signal 410 was switched between the left and right sides for a total period of 10.5 minutes, during which the reduced heart rate and blood pressure were substantially sustained.

These experiments demonstrate the effectiveness of the general approaches described previously, each of which involve a stimulus regimen to promote long term efficacy. These stimulus regimens generally involve reducing the output level of the baroreceptor activation device after the desired initial effect is established (first approach), alternating activation between two or more devices or output means positioned at different anatomical locations (second approach), and/or changing the time domain characteristics and/or the triggering event characteristics of the therapy (third approach). All of these approaches have the common objective of promoting long term efficacy by maintaining baroreflex responsiveness.

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreceptor activation device 70.

With general reference to FIGS. 4-21, schematic illustrations of specific embodiments of the baroreceptor activation device 70 are shown. The design, function and use of these specific embodiments, in addition to the control system 60 and sensor 80 (not shown), are the same as described with reference to FIG. 3, unless otherwise noted or apparent from the description. In addition, the anatomical features illustrated in FIGS. 4-20 are the same as discussed with reference to FIGS. 1, 2A and 2B, unless otherwise noted. In each embodiment, the connections between the components 60/70/80 may be physical (e.g., wires, tubes, cables, etc.) or remote (e.g., transmitter/receiver, inductive, magnetic, etc.). For physical connections, the connection may travel intraarterially, intravenously, subcutaneously, or through other natural tissue paths.

Figure 4B:
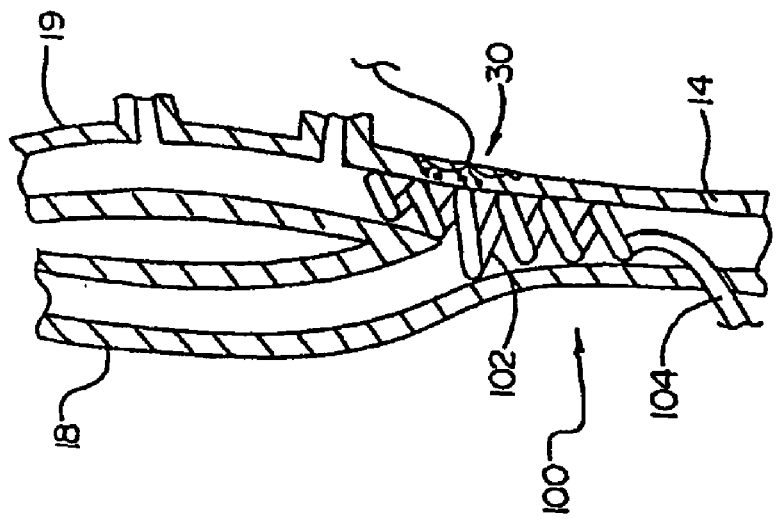
FIGS. 4A and 4B are schematic illustrations of a baroreceptor activation device in the form of an internal inflatable balloon which mechanically induces a baroreceptor signal in accordance with an embodiment of the present invention.
Figure 4A:
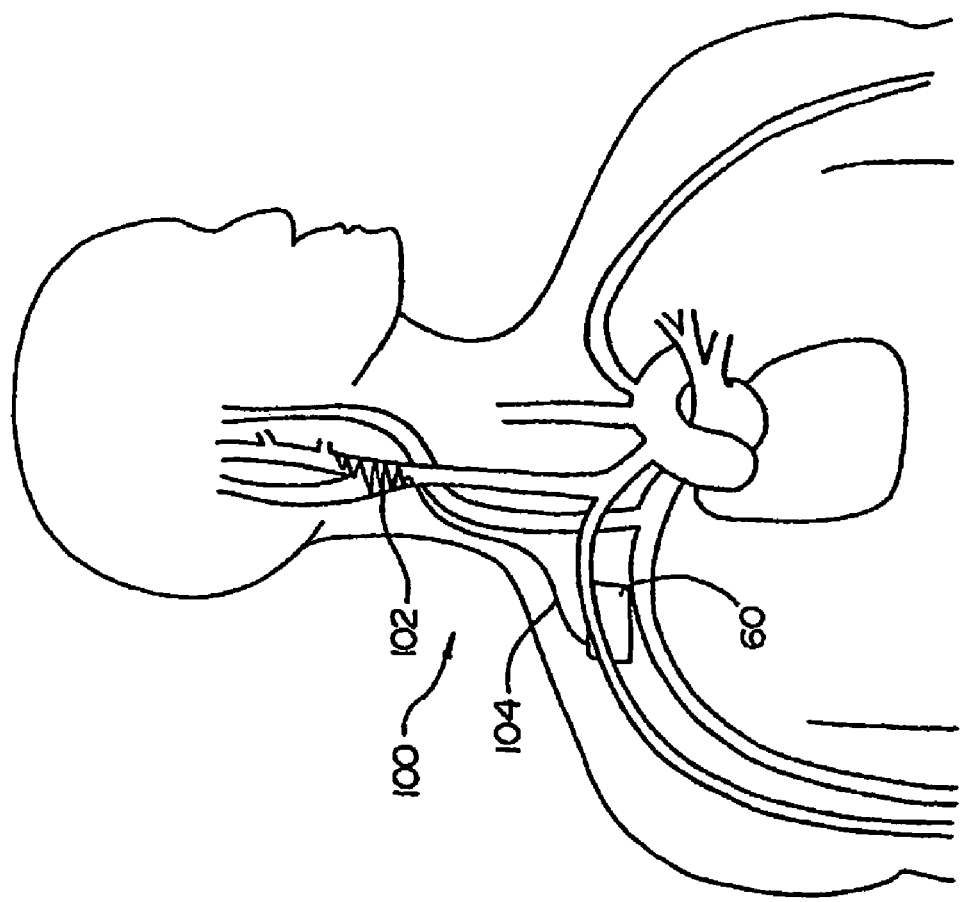

Refer now to FIGS. 4A and 4B which show schematic illustrations of a baroreceptor activation device 100 in the form of an intravascular inflatable balloon. The inflatable balloon device 100 includes a helical balloon 102 which is connected to a fluid line 104. An example of a similar helical balloon is disclosed in U.S. Pat. No. 5,181,911 to Shturman, the entire disclosure of which is hereby incorporated by reference. The balloon 102 preferably has a helical geometry or any other geometry which allows blood perfusion therethrough. The fluid line 104 is connected to the driver 66 of the control system 60. In this embodiment, the driver 66 comprises a pressure/vacuum source (i.e., an inflation device) which selectively inflates and deflates the helical balloon 102. Upon inflation, the helical balloon 102 expands, preferably increasing in outside diameter only, to mechanically activate baroreceptors 30 by stretching or otherwise deforming them and/or the vascular wall 40. Upon deflation, the helical balloon 102 returns to its relaxed geometry such that the vascular wall 40 returns to its nominal state. Thus, by selectively inflating the helical balloon 102, the baroreceptors 30 adjacent thereto may be selectively activated.

As an alternative to pneumatic or hydraulic expansion utilizing a balloon, a mechanical expansion device (not shown) may be used to expand or dilate the vascular wall 40 and thereby mechanically activate the baroreceptors 30. For example, the mechanical expansion device may comprise a tubular wire braid structure that diametrically expands when longitudinally compressed as disclosed in U.S. Pat. No. 5,222,971 to Willard et al., the entire disclosure of which is hereby incorporated by reference. The tubular braid may be disposed intravascularly and permits blood perfusion through the wire mesh. In this embodiment, the driver 66 may comprise a linear actuator connected by actuation cables to opposite ends of the braid. When the opposite ends of the tubular braid are brought closer together by actuation of the cables, the diameter of the braid increases to expand the vascular wall 40 and activate the baroreceptors 30.

Refer now to FIGS. 5A and 5B which show schematic illustrations of a baroreceptor activation device 120 in the form of an extravascular pressure cuff. The pressure cuff device 120 includes an inflatable cuff 122 which is connected to a fluid line 124. Examples of a similar cuffs 122 are disclosed in U.S. Pat. No. 4,256,094 to Kapp et al. and U.S. Pat. No. 4,881,939 to Newman, the entire disclosures of which are hereby incorporated by reference. The fluid line 124 is connected to the driver 66 of the control system 60. In this embodiment, the driver 66 comprises a pressure/vacuum source (i.e., an inflation device) which selectively inflates and deflates the cuff 122. Upon inflation, the cuff 122 expands, preferably increasing in inside diameter only, to mechanically activate baroreceptors 30 by stretching or otherwise deforming them and/or the vascular wall 40. Upon deflation, the cuff 122 returns to its relaxed geometry such that the vascular wall 40 returns to its nominal state. Thus, by selectively inflating the inflatable cuff 122, the baroreceptors 30 adjacent thereto may be selectively activated. The driver 66 may be automatically actuated by the control system 60 as discussed above, or may be manually actuated. An example of an externally manually actuated pressure/vacuum source is disclosed in U.S. Pat. No. 4,709,690 to Haber, the entire disclosure of which is hereby incorporated by reference. Examples of transdermally manually actuated pressure/vacuum sources are disclosed in U.S. Pat. No. 4,586,501 to Claracq, U.S. Pat. No. 4,828,544 to Lane et al., and U.S. Pat. No. 5,634,878 to Grundei et al., the entire disclosures of which are hereby incorporated by reference.

Those skilled in the art will recognize that other external compression devices may be used in place of the inflatable cuff device 120. For example, a piston actuated by a solenoid may apply compression to the vascular wall. An example of a solenoid actuated piston device is disclosed in U.S. Pat. No. 4,014,318 to Dokum et al, and an example of a hydraulically or pneumatically actuated piston device is disclosed in U.S. Pat. No. 4,586,501 to Claracq, the entire disclosures of which are hereby incorporated by reference. Other examples include a rotary ring compression device as disclosed in U.S. Pat. No. 4,551,862 to Haber, and an electromagnetically actuated compression ring device as disclosed in U.S. Pat. No. 5,509,888 to Miller, the entire disclosures of which are hereby incorporated by reference.

Refer now to FIGS. 6A and 6B which show schematic illustrations of a baroreceptor activation device 140 in the form of an intravascular deformable structure. The deformable structure device 140 includes a coil, braid or other stent-like structure 142 disposed in the vascular lumen. The deformable structure 142 includes one or more individual structural members connected to an electrical lead 144. Each of the structural members forming deformable structure 142 may comprise a shape memory material 146 (e.g., nickel titanium alloy) as illustrated in FIG. 6C, or a bimetallic material 148 as illustrated in FIG. 6D. The electrical lead 144 is connected to the driver 66 of the control system 60. In this embodiment, the driver 66 comprises an electric power generator or amplifier which selectively delivers electric current to the structure 142 which resistively heats the structural members 146/148. The structure 142 may be unipolar as shown using the surrounding tissue as ground, or bipolar or multipolar using leads connected to either end of the structure 142. Electrical power may also be delivered to the structure 142 inductively as described hereinafter with reference to FIGS. 14-16.

Upon application of electrical current to the shape memory material 146, it is resistively heated causing a phase change and a corresponding change in shape. Upon application of electrical current to the bimetallic material 148, it is resistively heated causing a differential in thermal expansion and a corresponding change in shape. In either case, the material 146/148 is designed such that the change in shape causes expansion of the structure 142 to mechanically activate baroreceptors 30 by stretching or otherwise deforming them and/or the vascular wall 40. Upon removal of the electrical current, the material 146/148 cools and the structure 142 returns to its relaxed geometry such that the baroreceptors 30 and/or the vascular wall 40 return to their nominal state. Thus, by selectively expanding the structure 142, the baroreceptors 30 adjacent thereto may be selectively activated.

Refer now to FIGS. 7A and 7B which show schematic illustrations of a baroreceptor activation device 160 in the form of an extravascular deformable structure. The extravascular deformable structure device 160 is substantially the same as the intravascular deformable structure device 140 described with reference to FIGS. 6A and 6B, except that the extravascular device 160 is disposed about the vascular wall, and therefore compresses, rather than expands, the vascular wall 40. The deformable structure device 160 includes a coil, braid or other stent-like structure 162 comprising one or more individual structural members connected to an electrical lead 164. Each of the structural members may comprise a shape memory material 166 (e.g., nickel titanium alloy) as illustrated in FIG. 7C, or a bimetallic material 168 as illustrated in FIG. 7D. The structure 162 may be unipolar as shown using the surrounding tissue as ground, or bipolar or multipolar using leads connected to either end of the structure 162. Electrical power may also be delivered to the structure 162 inductively as described hereinafter with reference to FIGS. 14-16.

Figure 8B:
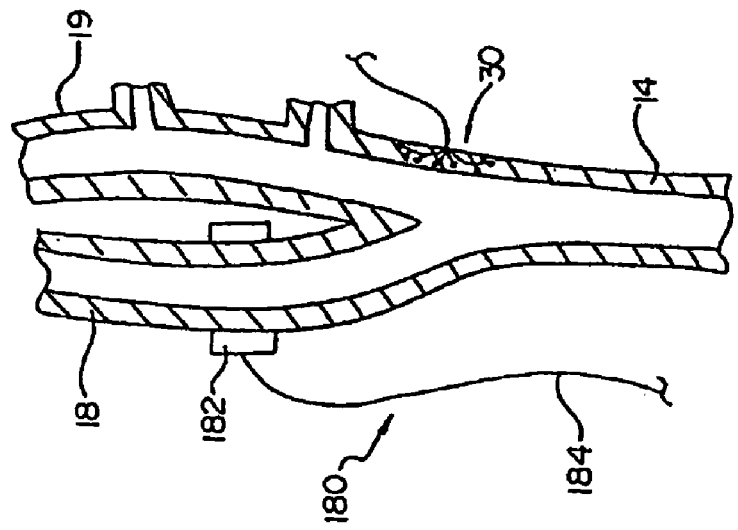
FIGS. 8A and 8B are schematic illustrations of a baroreceptor activation device in the form of an external flow regulator which artificially creates back pressure to induce a baroreceptor signal in accordance with an embodiment of the present invention.
Figure 8A:
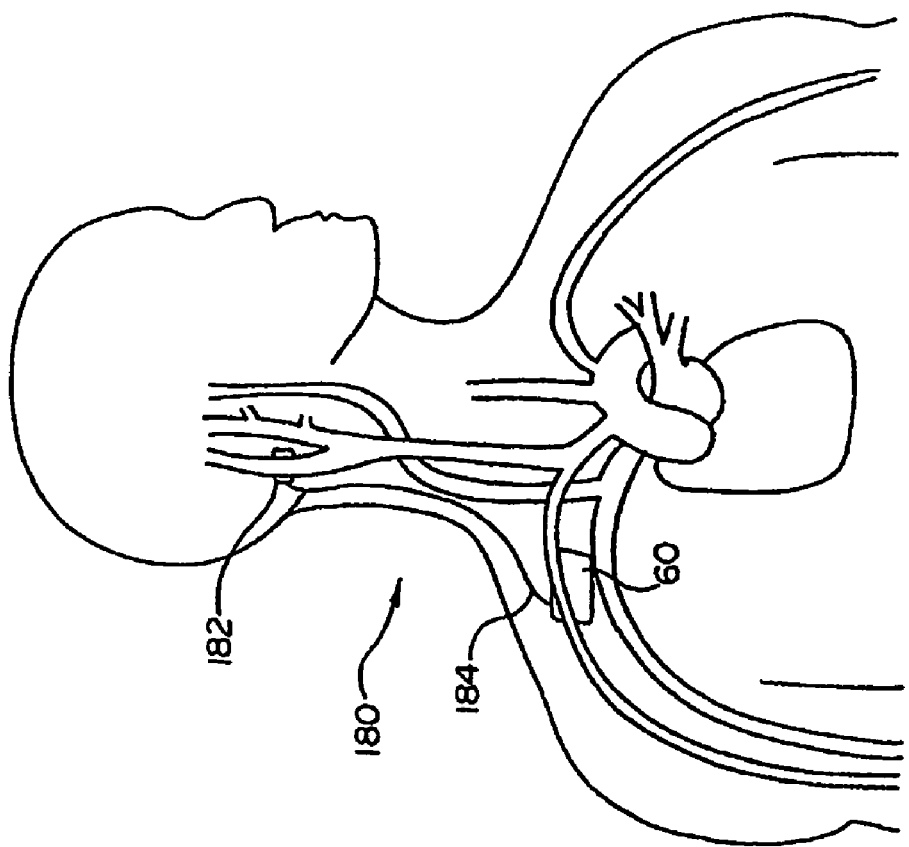

Upon application of electrical current to the shape memory material 166, it is resistively heated causing a phase change and a corresponding change in shape. Upon application of electrical current to the bimetallic material 168, it is resistively heated causing a differential in thermal expansion and a corresponding change in shape. In either case, the material 166/168 is designed such that the change in shape causes constriction of the structure 162 to mechanically activate baroreceptors 30 by compressing or otherwise deforming the baroreceptors 30 and/or the vascular wall 40. Upon removal of the electrical current, the material 166/168 cools and the structure 162 returns to its relaxed geometry such that the baroreceptors 30 and/or the vascular wall 40 return to their nominal state. Thus, by selectively compressing the structure 162, the baroreceptors 30 adjacent thereto may be selectively activated. Refer now to FIGS. 8A and 8B which show schematic illustrations of a baroreceptor activation device 180 in the form of an extravascular flow regulator which artificially creates back pressure adjacent the baroreceptors 30. The flow regulator device 180 includes an external compression device 182, which may comprise any of the external compression devices described with reference to FIGS. 5A and 5B. The external compression device 182 is operably connected to the driver 66 of the control system 60 by way of cable 184, which may comprise a fluid line or electrical lead, depending on the type of external compression device 182 utilized. The external compression device 182 is disposed about the vascular wall distal of the baroreceptors 30. For example, the external compression device 182 may be located in the distal portions of the external or internal carotid arteries 18/19 to create back pressure .adjacent to the baroreceptors 30 in the carotid sinus region 20. Alternatively, the external compression device 182 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

Figure 9B:
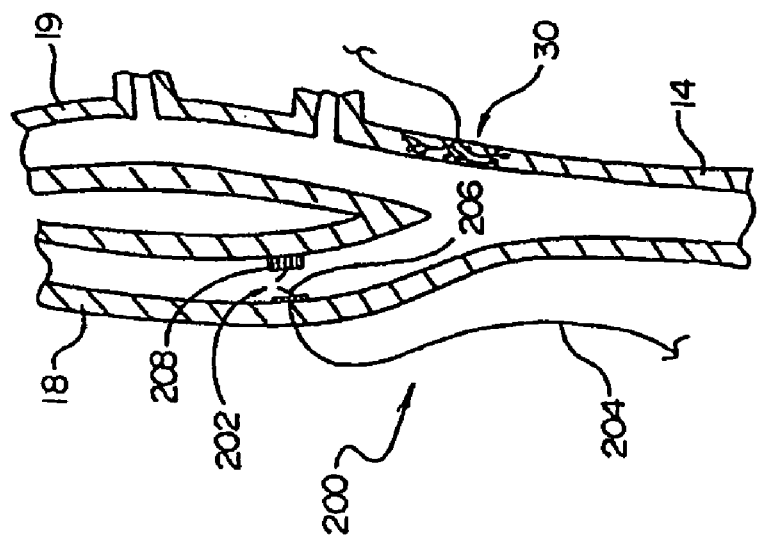
FIGS. 9A and 9B are schematic illustrations of a baroreceptor activation device in the form of an internal flow regulator which artificially creates back pressure to induce a baroreceptor signal in accordance with an embodiment of the present invention.
Figure 9A:
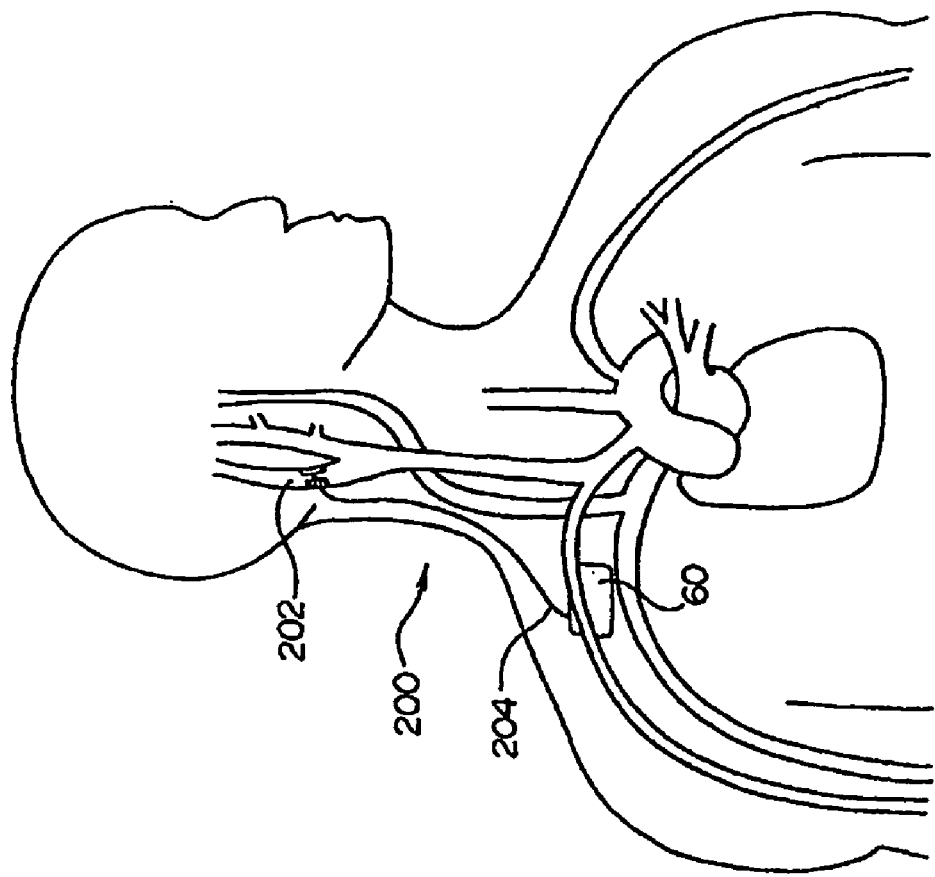

Upon actuation of the external compression device 182, the vascular wall is constricted thereby reducing the size of the vascular lumen therein. By reducing the size of the vascular lumen, pressure proximal of the external compression device 182 is increased thereby expanding the vascular wall. Thus, by selectively activating the external compression device 182 to constrict the vascular lumen and create back pressure, the baroreceptors 30 may be selectively activated. Refer now to FIGS. 9A and 9B which show schematic illustrations of a baroreceptor activation device 200 in the form of an intravascular flow regular which artificially creates back pressure adjacent the baroreceptors 30. The intravascular flow regulator device 200 is substantially similar in function and use as extravascular flow regulator 180 described with reference to FIGS. 8A and 8B, except that the intravascular flow regulator device 200 is disposed in the vascular lumen.

Intravascular flow regulator 200 includes an internal valve 202 to at least partially close the vascular lumen distal of the baroreceptors 30. By at least partially closing the vascular lumen distal of the baroreceptors 30, back pressure is created proximal of the internal valve 202 such that the vascular wall expands to activate the baroreceptors 30. The internal valve 202 may be positioned at any of the locations described with reference to the external compression device 182, except that the internal valve 202 is placed within the vascular lumen. Specifically, the internal compression device 202 may be located in the distal portions of the external or internal carotid arteries 18/19 to create back pressure adjacent to the baroreceptors 30 in the carotid sinus region 20. Alternatively, the internal compression device 202 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

The internal valve 202 is operably coupled to the driver 66 of the control system 60 by way of electrical lead 204. The control system 60 may selectively open, close or change the flow resistance of the valve 202 as described in more detail hereinafter. The internal valve 202 may include valve leaflets 206 (bi-leaflet or tri-leaflet) which rotate inside housing 208 about an axis between an open position and a closed position. The closed position may be completely closed or partially closed, depending on the desired amount of back pressure to be created. The opening and closing of the internal valve 202 may be selectively controlled by altering the resistance of leaflet 206 rotation or by altering the opening force of the leaflets 206. The resistance of rotation of the leaflets 206 may be altered utilizing electromagnetically actuated metallic bearings carried by the housing 208. The opening force of the leaflets 206 may be altered by utilizing electromagnetic coils in each of the leaflets to selectively magnetize the leaflets such that they either repel or attract each other, thereby facilitating valve opening and closing, respectively.

A wide variety of intravascular flow regulators may be used in place of internal valve 202. For example, internal inflatable balloon devices as disclosed in U.S. Pat. No. 4,682,583 to Burton et al. and U.S. Pat. No. 5,634,878 to Grundei et al., the entire disclosures of which is hereby incorporated by reference, may be adapted for use in place of valve 202. Such inflatable balloon devices may be operated in a similar manner as the inflatable cuff 122 described with reference to FIG. 5. Specifically, in this embodiment, the driver 66 would comprises a pressure/vacuum source (i.e., an inflation device) which selectively inflates and deflates the internal balloon. Upon inflation, the balloon expands to partially occlude blood flow and create back pressure to mechanically activate baroreceptors 30 by stretching or otherwise deforming them and/or the vascular wall 40. Upon deflation, the internal balloon returns to its normal profile such that flow is not hindered and back pressure is eliminated. Thus, by selectively inflating the internal balloon, the baroreceptors 30 proximal thereof may be selectively activated by creating back pressure.

Figure 10B:
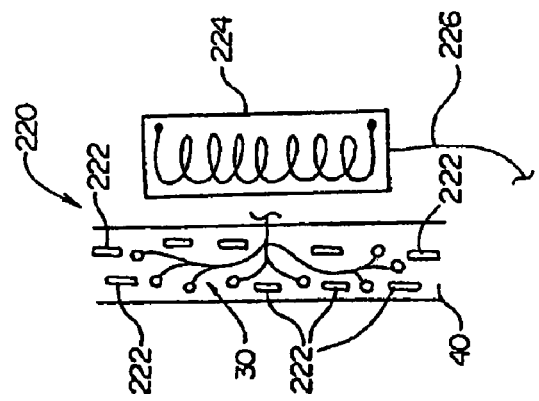
FIGS. 10A and 10B are schematic illustrations of a baroreceptor activation device in the form of a magnetic device which mechanically induces a baroreceptor signal in accordance with an embodiment of the present invention.
Figure 10A:
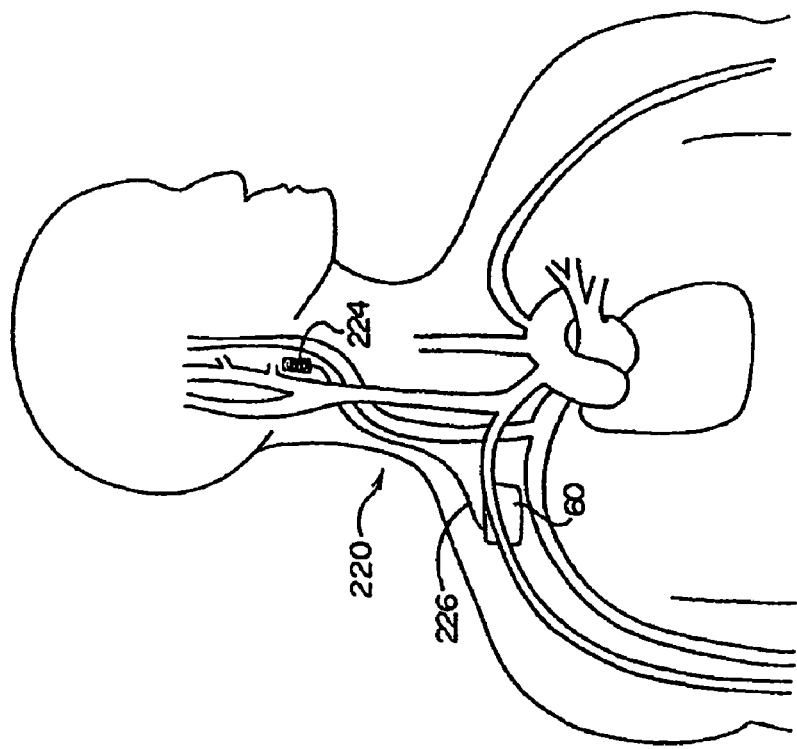

Refer now to FIGS. 10A and 10B which show schematic illustrations of a baroreceptor activation device 220 in the form of magnetic particles 222 disposed in the vascular wall 40. The magnetic particles 222 may comprise magnetically responsive materials (i.e., ferrous based materials) and may be magnetically neutral or magnetically active. Preferably, the magnetic particles 222 comprise permanent magnets having an elongate cylinder shape with north and south poles to strongly respond to magnetic fields. The magnetic particles 222 are actuated by an electromagnetic coil 224 which is operably coupled to the driver 66 of the control system 60 by way of an electrical cable 226. The electromagnetic coil 224 may be implanted as shown, or located outside the body, in which case the driver 66 and the remainder of the control system 60 would also be located outside the body. By selectively activating the electromagnetic coil 224 to create a magnetic field, the magnetic particles 222 may be repelled, attracted or rotated. Alternatively, the magnetic field created by the electromagnetic coil 224 may be alternated such that the magnetic particles 222 vibrate within the vascular wall 40. When the magnetic particles are repelled, attracted, rotated, vibrated or otherwise moved by the magnetic field created by the electromagnetic coil. 224, the baroreceptors 30 are mechanically activated.

The electromagnetic coil 224 is preferably placed as close as possible to the magnetic particles 222 in the vascular wall 40, and may be placed intravascularly, extravascularly, or in any of the alternative locations discussed with reference to inductor shown in FIGS. 14-16. The magnetic particles 222 may be implanted in the vascular wall 40 by injecting a ferro-fluid or a ferro-particle suspension into the vascular wall adjacent to the baroreceptors 30. To increase biocompatibility, the particles 222 may be coated with a ceramic, polymeric or other inert material. Injection of the fluid carrying the magnetic particles 222 is preferably performed percutaneously.

Figure 11B:
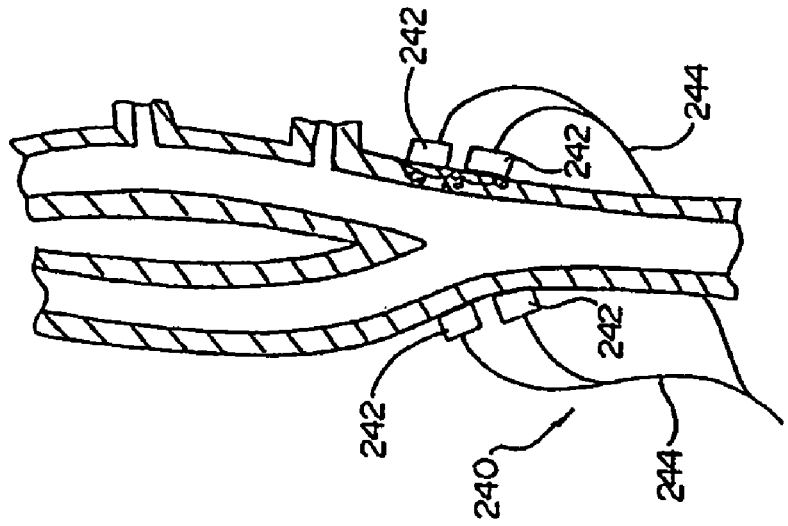
FIGS. 11A and 11B are schematic illustrations of a baroreceptor activation device in the form of a transducer which mechanically induces a baroreceptor signal in accordance with an embodiment of the present invention.
Figure 11A:
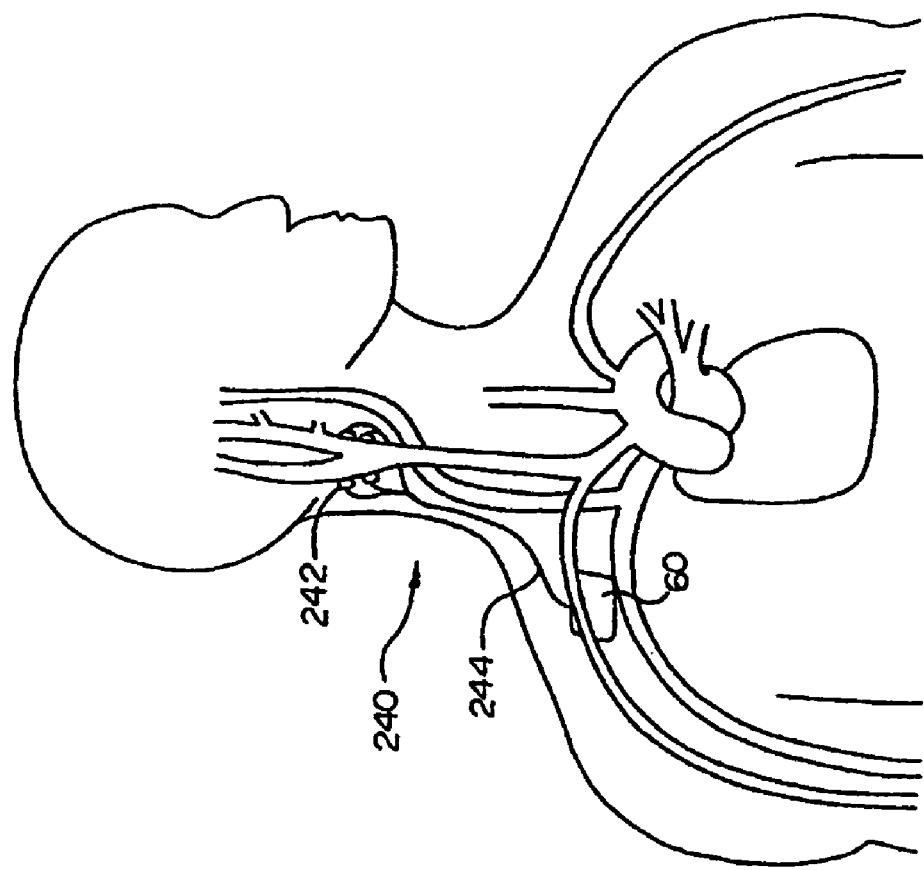

Refer now to FIGS. 11A and 11B which show schematic illustrations of a baroreceptor activation device 240 in the form of one or more transducers 242. Preferably, the transducers 242 comprise an array surrounding the vascular wall. The transducers 242 may be intravascularly or extravascularly positioned adjacent to the baroreceptors 30. In this embodiment, the transducers 242 comprise devices which convert electrical signals into some physical phenomena, such as mechanical vibration or acoustic waves. The electrical signals are provided to the transducers 242 by way of electrical cables 244 which are connected to the driver 66 of the control system 60. By selectively activating the transducers 242 to create a physical phenomena, the baroreceptors 30 may be mechanically activated.

Figure 12B:
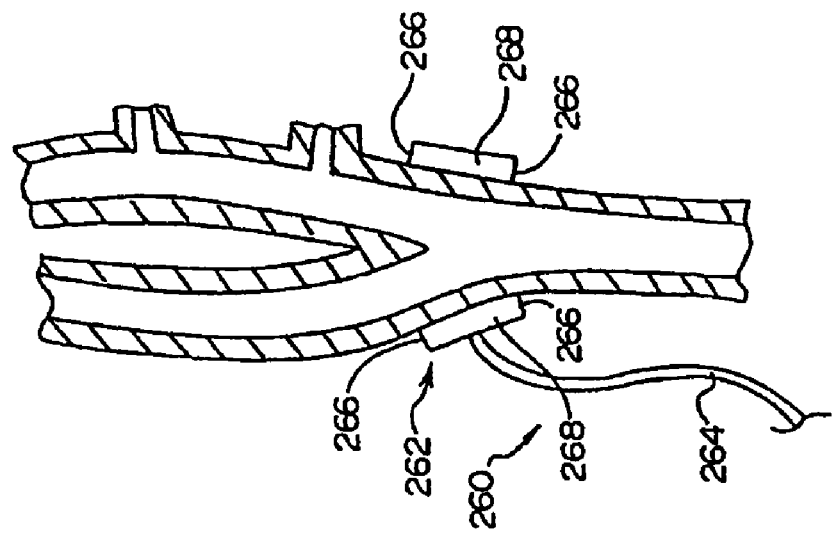
FIGS. 12A and 12B are schematic illustrations of a baroreceptor activation device in the form of a fluid delivery device which may be used to deliver an agent which chemically or biologically induces a baroreceptor signal in accordance with an embodiment of the present invention.
Figure 12A:
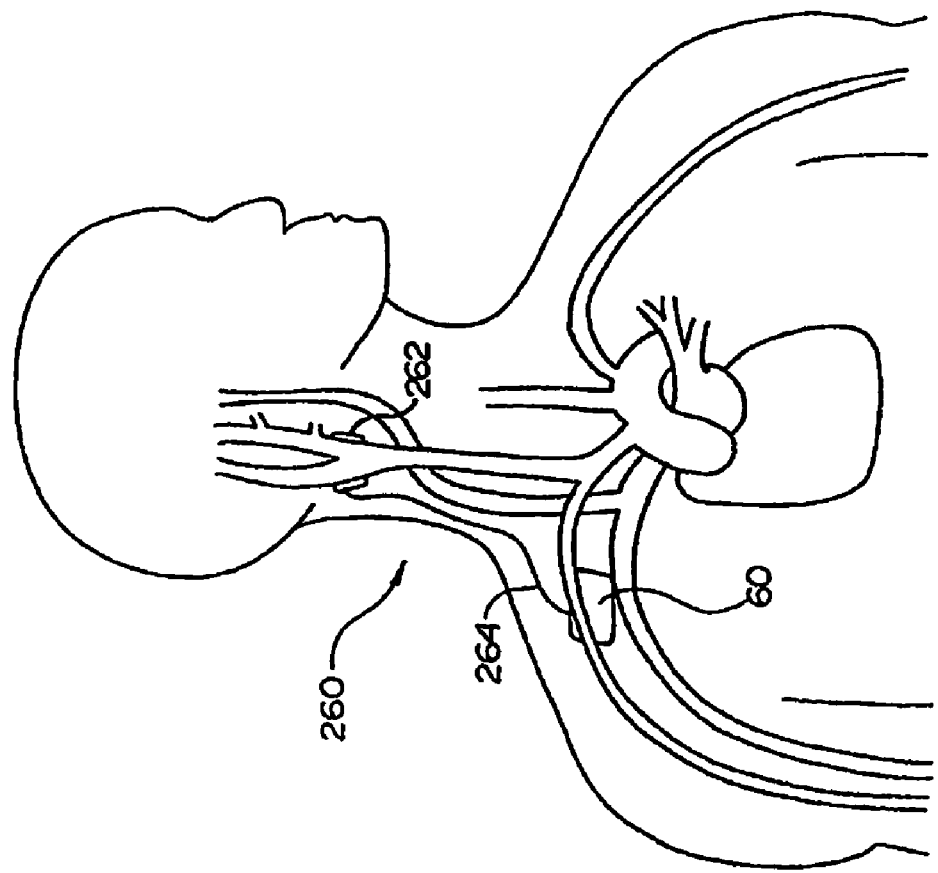

The transducers 242 may comprise an acoustic transmitter which transmits sonic or ultrasonic sound waves into the vascular wall 40 to activate the baroreceptors 30. Alternatively, the transducers 242 may comprise a piezoelectric material which vibrates the vascular wall to activate the baroreceptors 30. As a further alternative, the transducers 242 may comprise an artificial muscle which deflects upon application of an electrical signal. An example of an artificial muscle transducer comprises plastic impregnated with a lithium-perchlorate electrolyte disposed between sheets of polypyrrole, a conductive polymer. Such plastic muscles may be electrically activated to cause deflection in different directions depending on the polarity of the applied current. Refer now to FIGS. 12A and 12B which show schematic illustrations of a baroreceptor activation device 260 in the form of a local fluid delivery device 262 suitable for delivering a chemical or biological fluid agent to the vascular wall adjacent the baroreceptors 30. The local fluid delivery device 262 may be located intravascularly, extravascularly, or intramurally. For purposes of illustration only, the local fluid delivery device 262 is positioned extravascularly.

The local fluid delivery device 262 may include proximal and distal seals 266 which retain the fluid agent disposed in the lumen or cavity 268 adjacent to vascular wall. Preferably, the local fluid delivery device 262 completely surrounds the vascular wall 40 to maintain an effective seal. Those skilled in the art will recognize that the local fluid delivery device 262 may comprise a wide variety of implantable drug delivery devices or pumps known in the art.

The local fluid delivery device 260 is connected to a fluid line 264 which is connected to the driver 66 of the control system 60. In this embodiment, the driver 66 comprises a pressure/vacuum source and fluid reservoir containing the desired chemical or biological fluid agent. The chemical or biological fluid agent may comprise a wide variety of stimulatory substances. Examples include veratridine, bradykinin, prostaglandins, and related substances. Such stimulatory substances activate the baroreceptors 30 directly or enhance their sensitivity to other stimuli and therefore may be used in combination with the other baroreceptor activation devices described herein. Other examples include growth factors and other agents that modify the function of the baroreceptors 30 or the cells of the vascular tissue surrounding the baroreceptors 30 causing the baroreceptors 30 to be activated or causing alteration of their responsiveness or activation pattern to other stimuli. It is also contemplated that injectable stimulators that are induced remotely, as described in U.S. Pat. No. 6,061,596 which is incorporated herein by reference, may be used with the present invention.

As an alternative, the fluid delivery device 260 may be used to deliver a photochemical that is essentially inert until activated by light to have a stimulatory effect as described above. In this embodiment, the fluid delivery device 260 would include a light source such as a light emitting diode (LED), and the driver 66 of the control system 60 would include a pulse generator for the LED combined with a pressure/vacuum source and fluid reservoir described previously. The photochemical would be delivered with the fluid delivery device 260 as described above, and the photochemical would be activated, deactivated or modulated by activating, deactivating or modulating the LED.

As a further alternative, the fluid delivery device 260 may be used to deliver a warm or hot fluid (e.g. saline) to thermally activate the baroreceptors 30. In this embodiment, the driver 66 of the control system 60 would include a heat generator for heating the fluid, combined with a pressure/vacuum source and fluid reservoir described previously. The hot or warm fluid would be delivered and preferably circulated with the fluid delivery device 260 as described above, and the temperature of the fluid would be controlled by the driver 66.

Refer now to FIGS. 13A and 13B which show schematic illustrations of a baroreceptor activation device 280 in the form of an intravascular electrically conductive structure or electrode 282. The electrode structure 282 may comprise a self-expanding or balloon expandable coil, braid or other stent-like structure disposed in the vascular lumen. The electrode structure 282 may serve the dual purpose of maintaining lumen patency while also delivering electrical stimuli. To this end, the electrode structure 282 may be implanted utilizing conventional intravascular stent and filter delivery techniques. Preferably, the electrode structure 282 comprises a geometry which allows blood perfusion therethrough. The electrode structure 282 comprises electrically conductive material which may be selectively insulated to establish contact with the inside surface of the vascular wall 40 at desired locations, and limit extraneous electrical contact with blood flowing through the vessel and other tissues.

The electrode structure 282 is connected to electric lead 284 which is connected to the driver 66 of the control system 60. The driver 66, in this embodiment, may comprise a power amplifier, pulse generator or the like to selectively deliver electrical control signals to structure 282. As mentioned previously, the electrical control signal generated by the driver 66 may be continuous, periodic, episodic or a combination thereof, as dictated by an algorithm contained in memory 62 of the control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

By selectively activating, deactivating or otherwise modulating the electrical control signal transmitted to the electrode structure 282, electrical energy may be delivered to the vascular wall to activate the baroreceptors 30. As discussed previously, activation of the baroreceptors 30 may occur directly or indirectly. In particular, the electrical signal delivered to the vascular wall 40 by the electrode structure 282 may cause the vascular wall to stretch or otherwise deform thereby indirectly activating the baroreceptors 30 disposed therein. Alternatively, the electrical signals delivered to the vascular wall by the electrode structure 282 may directly activate the baroreceptors 30 by changing the electrical potential across the baroreceptors 30. In either case, the electrical signal is delivered to the vascular wall 40 immediately adjacent to the baroreceptors 30. It is also contemplated that the electrode structure 282 may delivery thermal energy by utilizing a semi-conductive material having a higher resistance such that the electrode structure 282 resistively generates heat upon application of electrical energy.

Figure 21B:
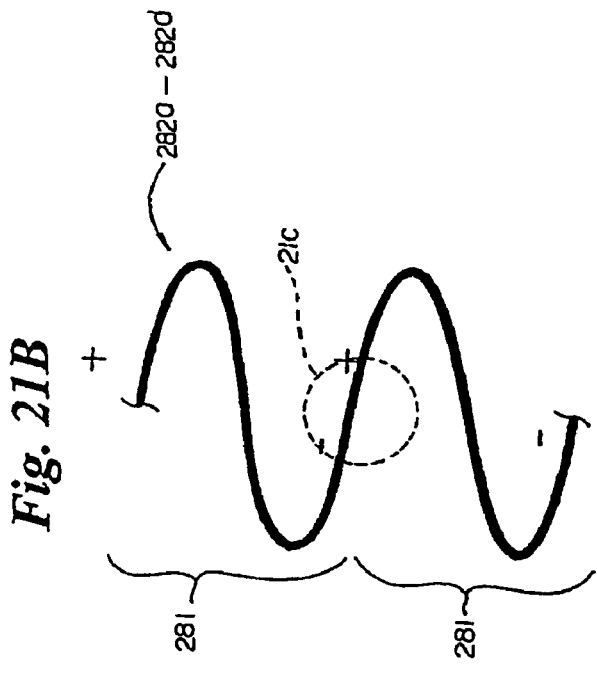
FIGS. 21A-21C are schematic illustrations of a preferred embodiment of an inductively activated electrically conductive structure.
Figure 21C:
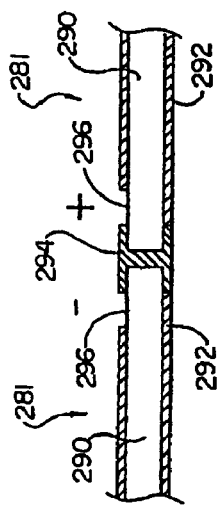
Figure 21A:
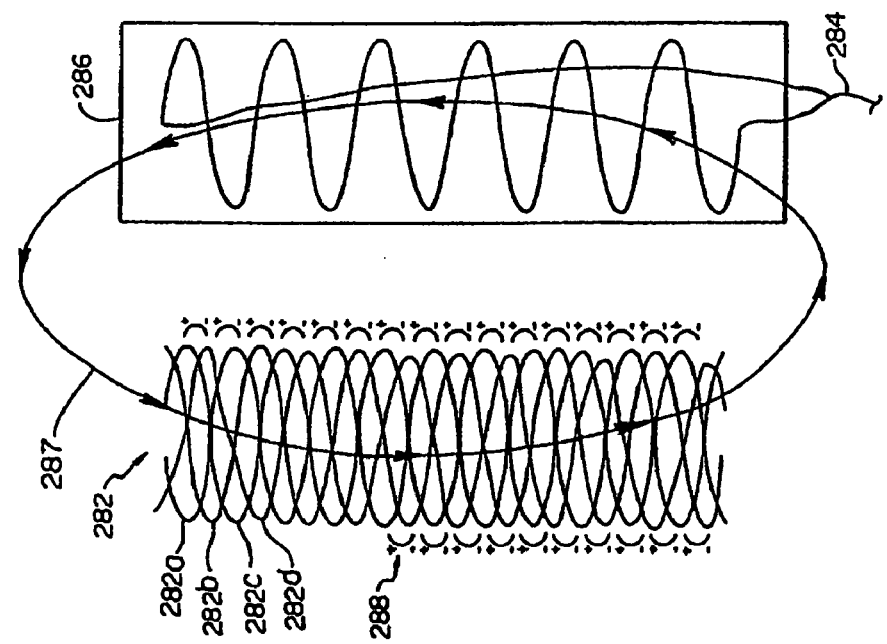

Various alternative embodiments are contemplated for the electrode structure 282, including its design, implanted location, and method of electrical activation. For example, the electrode structure 282 may be unipolar as shown in FIGS. 13A and 13B using the surrounding tissue as ground, or bipolar using leads connected to either end of the structure 282 as shown in FIGS. 18A and 18B. In the embodiment of FIGS. 18A and 18B, the electrode structure 282 includes two or more individual electrically conductive members 283/285 which are electrically isolated at their respective cross-over points utilizing insulative materials. Each of the members 283/285 is connected to a separate conductor contained within the electrical lead 284. Alternatively, an array of bipoles may be used as described in more detail with reference to FIG. 21. As a further alternative, a multipolar arrangement may be used wherein three or more electrically conductive members are included in the structure 282. For example, a tripolar arrangement may be provided by one electrically conductive member having a polarity disposed between two electrically conductive members having the opposite polarity. In terms of electrical activation, the electrical signals may be directly delivered to the electrode structure 282 as described with reference to FIGS. 13A and 13B, or indirectly delivered utilizing an inductor as illustrated in FIGS. 14-16 and 21. The embodiments of FIGS. 14-16 and 21 utilize an inductor 286 which is operably connected to the driver 66 of the control system 60 by way of electrical lead 284. The inductor 286 comprises an electrical winding which creates a magnetic field 287 (as seen in FIG. 21) around the electrode structure 282. The magnetic field 287 may be alternated by alternating the direction of current flow through the inductor 286. Accordingly, the inductor 286 may be utilized to create current flow in the electrode structure 282 to thereby deliver electrical signals to the vascular wall 40 to directly or indirectly activate the baroreceptors 30. In all embodiments, the inductor 286 may be covered with an electrically insulative material to eliminate direct electrical stimulation of tissues surrounding the inductor 286. A preferred embodiment of an inductively activated electrode structure 282 is described in more detail with reference to FIGS. 21A-21C.

The embodiments of FIGS. 13-16 may be modified to form a cathode/anode arrangement. Specifically, the electrical inductor 286 would be connected to the driver 66 as shown in FIGS. 14-16 and the electrode structure 282 would be connected to the driver 66 as shown in FIG. 13. With this arrangement, the electrode structure 282 and the inductor 286 may be any suitable geometry and need not be coiled for purposes of induction. The electrode structure 282 and the inductor 286 would comprise a cathode/anode or anode/cathode pair. For example, when activated, the cathode 282 may generate a primary stream of electrons which travel through the inter-electrode space (i.e., vascular tissue and baroreceptors 30) to the anode 286. The cathode is preferably cold, as opposed to thermionic, during electron emission. The electrons may be used to electrically or thermally activate the baroreceptors 30 as discussed previously.

Figure 15A:
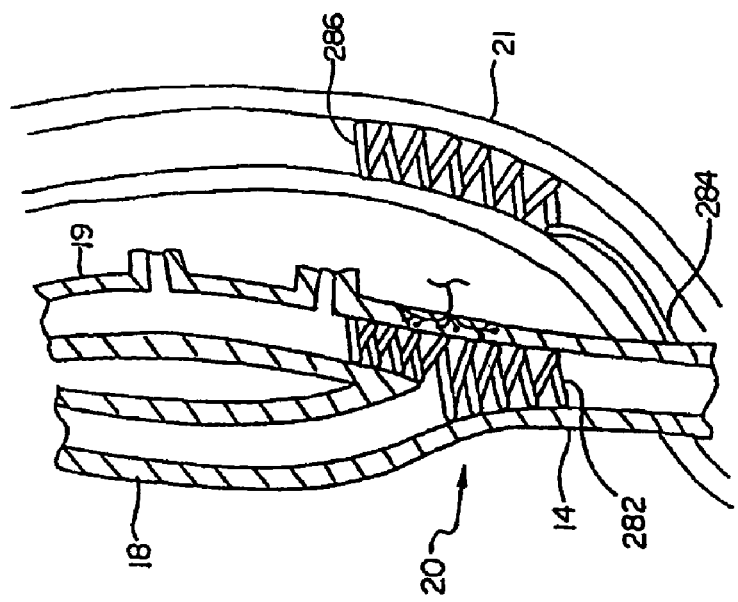
FIGS. 15A and 15B are schematic illustrations of a baroreceptor activation device in the form of an internal conductive structure, activated by an internal inductor located in an adjacent vessel, which electrically or thermally induces a baroreceptor signal in accordance with an embodiment of the present invention.
Figure 15B:
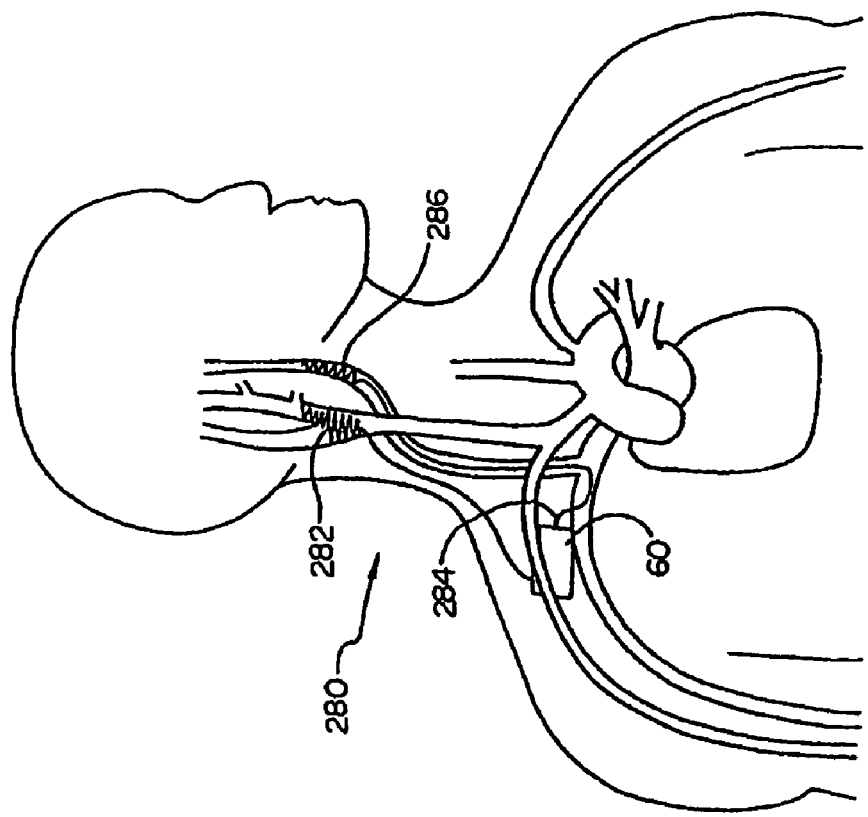

The electrical inductor 286 is preferably disposed as close as possible to the electrode structure 282. For example, the electrical inductor 286 may be disposed adjacent the vascular wall as illustrated in FIGS. 14A and 14B. Alternatively, the inductor 286 may be disposed in an adjacent vessel as illustrated in FIGS. 15A and 15B. If the electrode structure 282 is disposed in the carotid sinus 20, for example, the inductor 286 may be disposed in the internal jugular vein 21 as illustrated in FIGS. 15A and 15B. In the embodiment of FIGS. 15A and 15B, the electrical inductor 286 may comprise a similar structure as the electrode structure 282. As a further alternative, the electrical inductor 286 may be disposed outside the patient's body, but as close as possible to the electrode structure 282. If the electrode structure 282 is disposed in the carotid sinus 20, for example, the electrical inductor 286 may be disposed on the right or left side of the neck of the patient as illustrated in FIGS. 16A and 16B. In the embodiment of FIGS. 16A and 16B, wherein the electrical inductor 286 is disposed outside the patient's body, the control system 60 may also be disposed outside the patient's body.

Figure 17B:
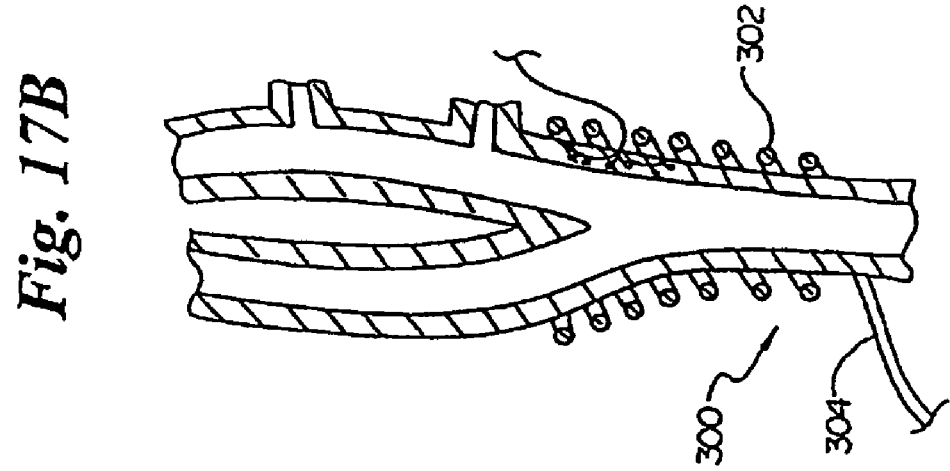
FIGS. 17A and 17B are schematic illustrations of a baroreceptor activation device in the form of an external conductive structure which electrically or thermally induces a baroreceptor signal in accordance with an embodiment of the present invention.
Figure 17A:
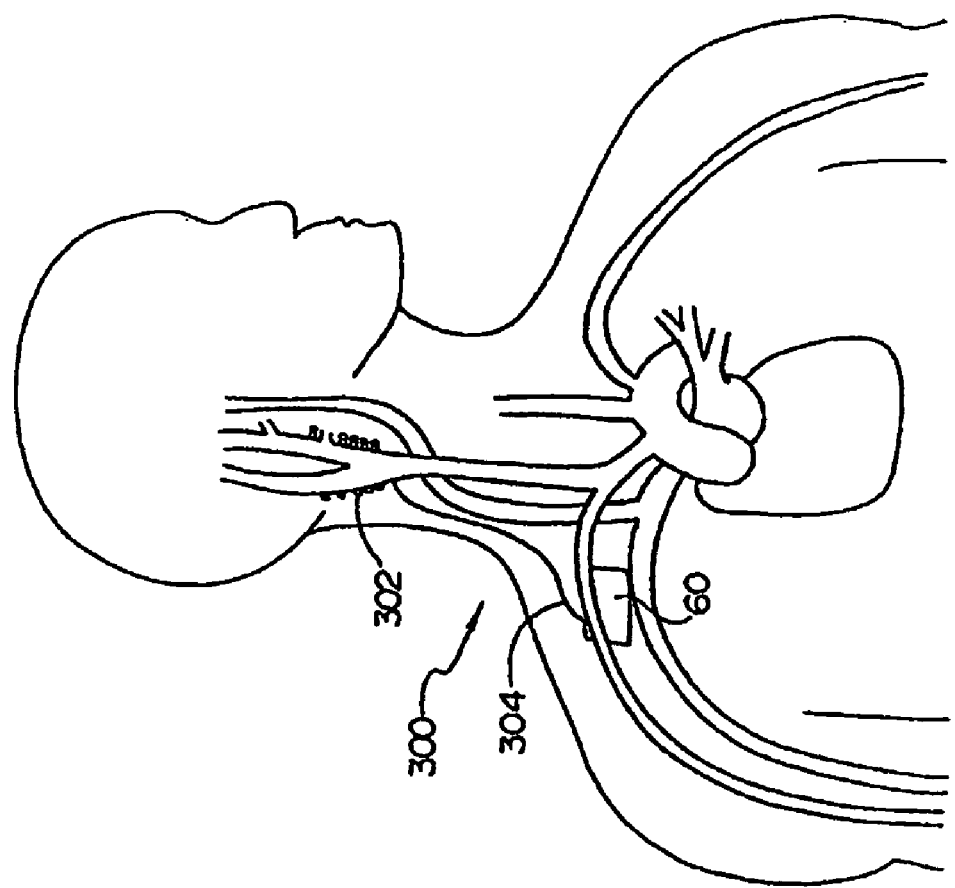

In terms of implant location, the electrode structure 282 may be intravascularly disposed as described with reference to FIGS. 13A and 13B, or extravascularly disposed as described with reference to FIGS. 17A and 17B, which show schematic illustrations of a baroreceptor activation device 300 in the form of an extravascular electrically conductive structure or electrode 302. Except as described herein, the extravascular electrode structure 302 is the same in design, function, and use as the intravascular electrode structure 282. The electrode structure 302 may comprise a coil, braid or other structure capable of surrounding the vascular wall. Alternatively, the electrode structure 302 may comprise one or more electrode patches distributed around the outside surface of the vascular wall. Because the electrode structure 302 is disposed on the outside surface of the vascular wall, intravascular delivery techniques may not be practical, but minimally invasive surgical techniques will suffice. The extravascular electrode structure 302 may receive electrical signals directly from the driver 66 of the control system 60 by way of electrical lead 304, or indirectly by utilizing an inductor (not shown) as described with reference to FIGS. 14-16.

Figure 19B:
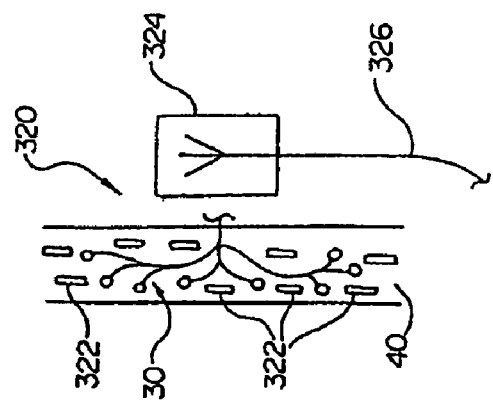
FIGS. 19A and 19B are schematic illustrations of a baroreceptor activation device in the form of an electromagnetic field responsive device which electrically or thermally induces a baroreceptor signal in accordance with an embodiment of the present invention.
Figure 19A:
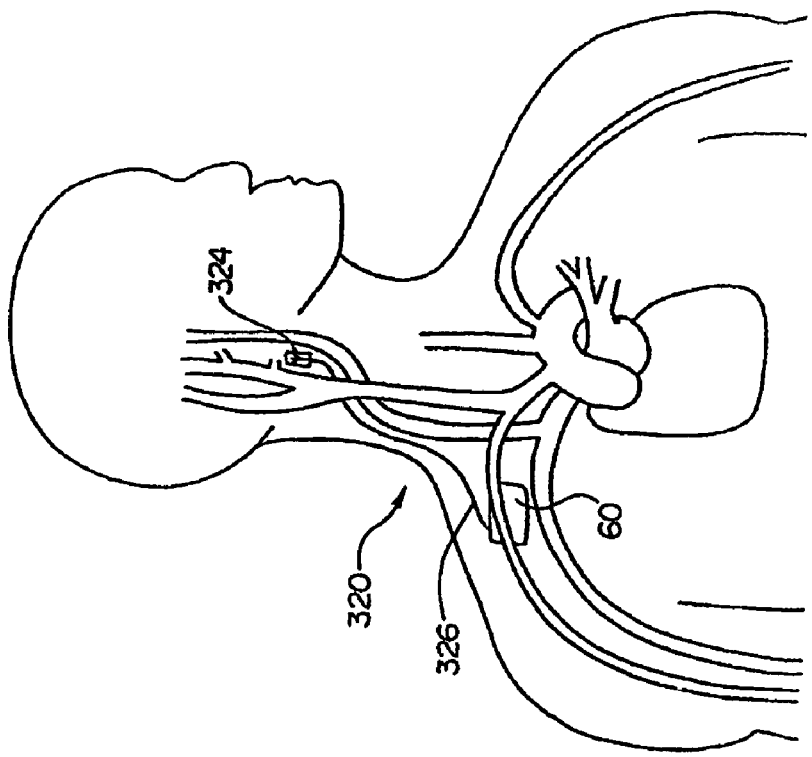

Refer now to FIGS. 19A and 19B which show schematic illustrations of a baroreceptor activation device 320 in the form of electrically conductive particles 322 disposed in the vascular wall. This embodiment is substantially the same as the embodiments described with reference to FIGS. 13-18, except that the electrically conductive particles 322 are disposed within the vascular wall, as opposed to the electrically conductive structures 282/302 which are disposed on either side of the vascular wall. In addition, this embodiment is similar to the embodiment described with reference to FIG. 10, except that the electrically conductive particles 322 are not necessarily magnetic as with magnetic particles 222, and the electrically conductive particles 322 are driven by an electromagnetic filed rather than by a magnetic field.

In this embodiment, the driver 66 of the control system 60 comprises an electromagnetic transmitter such as an radiofrequency or microwave transmitter. Electromagnetic radiation is created by the transmitter 66 which is operably coupled to an antenna 324 by way of electrical lead 326. Electromagnetic waves are emitted by the antenna 324 and received by the electrically conductive particles 322 disposed in the vascular wall 40. Electromagnetic energy creates oscillating current flow within the electrically conductive particles 322, and depending on the intensity of the electromagnetic radiation and the resistivity of the conductive particles 322, may cause the electrical particles 322 to generate heat. The electrical or thermal energy generated by the electrically conductive particles 322 may directly activate the baroreceptors 30, or indirectly activate the baroreceptors 30 by way of the surrounding vascular wall tissue.

The electromagnetic radiation transmitter 66 and antenna 324 may be disposed in the patient's body, with the antenna 324 disposed adjacent to the conductive particles in the vascular wall 40 as illustrated in FIGS. 19A and 19B. Alternatively, the antenna 324 may be disposed in any of the positions described with reference to the electrical inductor shown in FIGS. 14-16. It is also contemplated that the electromagnetic radiation transmitter 66 and antenna 324 may be utilized in combination with the intravascular and extravascular electrically conductive structures 282/302 described with reference to FIGS. 13-18 to generate thermal energy on either side of the vascular wall.

As an alternative, the electromagnetic radiation transmitter 66 and antenna 324 may be used without the electrically conductive particles 322. Specifically, the electromagnetic radiation transmitter 66 and antenna 324 may be used to deliver electromagnetic radiation (e.g., RF, microwave) directly to the baroreceptors 30 or the tissue adjacent thereto to cause localized heating, thereby thermally inducing a baroreceptor 30 signal.

Figure 20B:
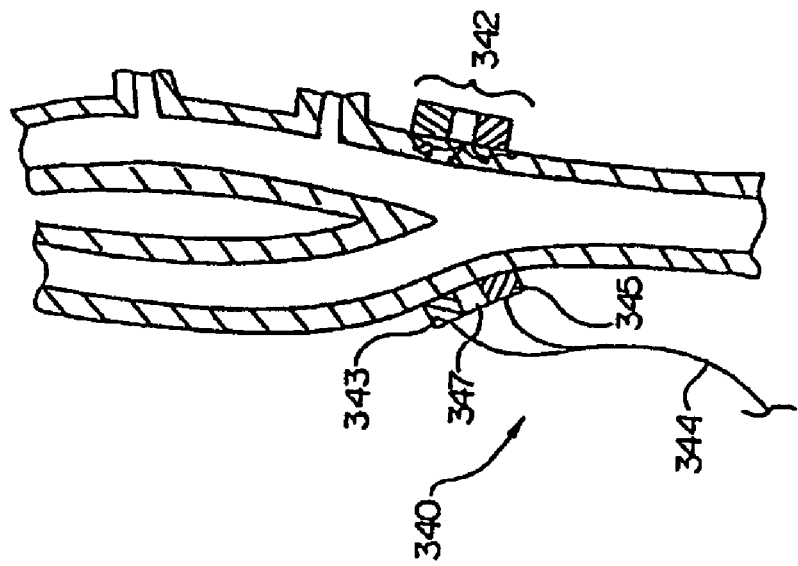
FIGS. 20A and 20B are schematic illustrations of a baroreceptor activation device in the form of an external Peltier device which thermally induces a baroreceptor signal in accordance with an embodiment of the present invention.
Figure 20A:
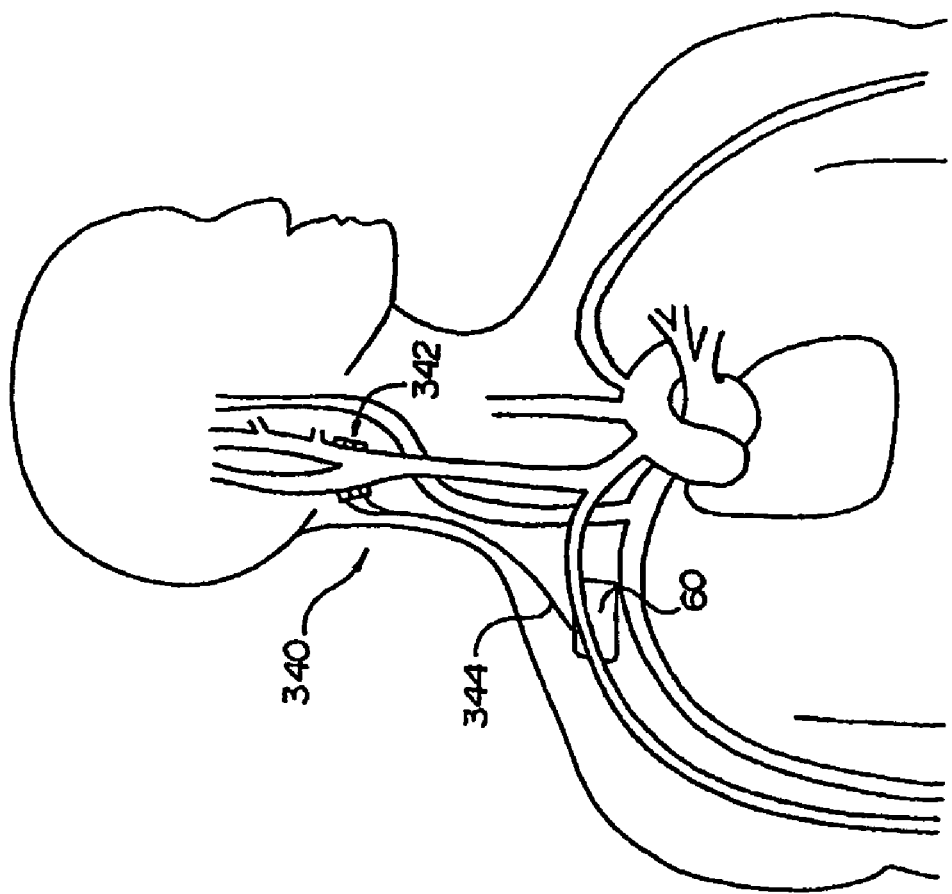

Refer now to FIGS. 20A and 20B which show schematic illustrations of a baroreceptor activation device 340 in the form of a Peltier effect device 342. The Peltier effect device 342 may be extravascularly positioned as illustrated, or may be intravascularly positioned similar to an intravascular stent or filter. The Peltier effect device 342 is operably connected to the driver 66 of the control system 60 by way of electrical lead 344. The Peltier effect device 342 includes two dissimilar metals or semiconductors 343/345 separated by a thermal transfer junction 347. In this particular embodiment, the driver 66 comprises a power source which delivers electrical energy to the dissimilar metals or semiconductors 343/345 to create current flow across the thermal junction 347.

When current is delivered in an appropriate direction, a cooling effect is created at the thermal junction 347. There is also a heating effect created at the junction between the individual leads 344 connected to the dissimilar metals or semiconductors 343/345. This heating effect, which is proportional to the cooling effect, may be utilized to activate the baroreceptors 30 by positioning the junction between the electrical leads 344 and the dissimilar metals or semiconductors 343/345 adjacent to the vascular wall 40.

Refer now to FIGS. 21A-21C which show schematic illustrations of a preferred embodiment of an inductively activated electrode structure 282 for use with the embodiments described with reference to FIGS. 14-16. In this embodiment, current flow in the electrode structure 282 is induced by a magnetic field 287 created by an inductor 286 which is operably coupled to the driver 66 of the control system 60 by way of electrical cable 284. The electrode structure 282 preferably comprises a multi-filar self-expanding braid structure including a plurality of individual members 282a, 282b, 282c and 282d. However, the electrode structure 282 may simply comprise a single coil for purposes of this embodiment. Each of the individual coil members 282a-282d comprising the electrode structure 282 consists of a plurality of individual coil turns 281 connected end to end as illustrated in FIGS. 21B and 21C. FIG. 21C is a detailed view of the connection between adjacent coil turns 281 as shown in FIG. 21B. Each coil turn 281 comprises electrically isolated wires or receivers in which a current flow is established when a changing magnetic field 287 is created by the inductor 286. The inductor 286 is preferably covered with an electrically insulative material to eliminate direct electrical stimulation of tissues surrounding the inductor 286. Current flow through each coil turn 281 results in a potential drop 288 between each end of the coil turn 281. With a potential drop defined at each junction between adjacent coil turns 281, a localized current flow cell is created in the vessel wall adjacent each junction. Thus an array or plurality of bipoles are created by the electrode structure 282 and uniformly distributed around the vessel wall. Each coil turn 281 comprises an electrically conductive wire material 290 surrounded by an electrically insulative material 292. The ends of each coil turn 281 are connected by an electrically insulated material 294 such that each coil turn 281 remains electrically isolated. The insulative material 294 mechanically joins but electrically isolates adjacent coil turns 281 such that each turn 281 responds with a similar potential drop 288 when current flow is induced by the changing magnetic field 287 of the inductor 286. An exposed portion 296 is provided at each end of each coil turn 281 to facilitate contact with the vascular wall tissue. Each exposed portion 296 comprises an isolated electrode in contact with the vessel wall. The changing magnetic field 287 of the inductor 286 causes a potential drop in each coil turn 281 thereby creating small current flow cells in the vessel wall corresponding to adjacent exposed regions 296. The creation of multiple small current cells along the inner wall of the blood vessel serves to create a cylindrical zone of relatively high current density such that the baroreceptors 30 are activated. However, the cylindrical current density field quickly reduces to a negligible current density near the outer wall of the vascular wall, which serves to limit extraneous current leakage to minimize or eliminate unwanted activation of extravascular tissues and structures such as nerves or muscles.

To address low blood pressure and other conditions requiring blood pressure augmentation, some of the baroreceptor activation devices described previously may be used to selectively and controllably regulate blood pressure by inhibiting or dampening baroreceptor signals. By selectively and controllably inhibiting or dampening baroreceptor signals, the present invention reduces conditions associated with low blood pressure as described previously. Specifically, the present invention would function to increase the blood pressure and level of sympathetic nervous system activation by inhibiting or dampening the activation of baroreceptors.

This may be accomplished by utilizing mechanical, thermal, electrical and chemical or biological means. Mechanical means may be triggered off the pressure pulse of the heart to mechanically limit deformation of the arterial wall. For example, either of the external compression devices 120/160 described previously may be used to limit deformation of the arterial wall. Alternatively, the external compression device may simply limit diametrical expansion of the vascular wall adjacent the baroreceptors without the need for a trigger or control signal.

Thermal means may be used to cool the baroreceptors 30 and adjacent tissue to reduce the responsiveness of the baroreceptors 30 and thereby dampen baroreceptor signals. Specifically, the baroreceptor 30 signals may be dampened by either directly cooling the baroreceptors 30, to reduce their sensitivity, metabolic activity and function, or by cooling the surrounding vascular wall tissue thereby causing the wall to become less responsive to increases in blood pressure. An example of this approach is to use the cooling effect of the Peltier device 340. Specifically, the thermal transfer junction 347 may be positioned adjacent the vascular wall to provide a cooling effect. The cooling effect may be used to dampen signals generated by the baroreceptors 30. Another example of this approach is to use the fluid delivery device 260 to deliver a cool or cold fluid (e.g. saline). In this embodiment, the driver 66 would include a heat exchanger to cool the fluid and the control system 60 may be used to regulate the temperature of the fluid, thereby regulating the degree of baroreceptor 30 signal dampening.

Electrical means may be used to inhibit baroreceptor 30 activation by, for example, hyperpolarizing cells in or adjacent to the baroreceptors 30. Examples of devices and method of hyperpolarizing cells are disclosed in U.S. Pat. No. 5,814,079 to Kieval, and U.S. Pat. No. 5,800,464 to Kieval, the entire disclosures of which are hereby incorporated by reference. Such electrical means may be implemented using any of the embodiments discussed with reference to FIGS. 13-18 and 21.

Chemical or biological means may be used to reduce the sensitivity of the baroreceptors 30. For example, a substance that reduces baroreceptor sensitivity may be delivered using the fluid delivery device 260 described previously. The desensitizing agent may comprise, for example, tetrodotoxin or other inhibitor of excitable tissues. From the foregoing, it should be apparent to those skilled in the art that the present invention provides a number of devices, systems and methods by which the blood pressure, nervous system activity, and neurohormonal activity may be selectively and controllably regulated by activating baroreceptors or by inhibiting/dampening baroreceptor signals. Thus, the present invention may be used to increase or decrease blood pressure, sympathetic nervous system activity and neurohormonal activity, as needed to minimize deleterious effects on the heart, vasculature and other organs and tissues.

The baroreceptor activation devices described previously may also be used to provide antiarrhythmic effects. It is well known that the susceptibility of the myocardium to the development of conduction disturbances and malignant cardiac arrhythmias is influenced by the balance between sympathetic and parasympathetic nervous system stimulation to the heart. That is, heightened sympathetic nervous system activation, coupled with decreased parasympathetic stimulation, increases the irritability of the myocardium and likelihood of an arrhythmia. Thus, by decreasing the level of sympathetic nervous system activation and enhancing the level of parasympathetic activation, the devices, systems and methods of the current invention may be used to provide a protective effect against the development of cardiac conduction disturbances.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of inducing a baroreceptor signal to effect a change in the baroreflex system in a patient, the method comprising the steps of:

providing a baroreceptor activation device including a first means for outputting an electrical signal to electrically induce a baroreceptor signal and a second means for outputting an electrical signal to electrically induce a baroreceptor signal, the first means for outputting an electrical signal adapted to be positioned proximate a first baroreceptor location and the second means for outputting an electrical signal adapted to be positioned proximate a second baroreceptor location; and alternating the electrical signal between the first means for outputting and the second means for outputting to promote long term efficacy of inducing baroreceptor signals and reduce exposure of a single baroreceptor location.

2. A method as in claim 1, wherein the electrical signal comprises a series of pulses, and wherein the step of causing the electrical signals to be changed further comprises causing a pulse characteristic of the electrical signal to be changed, the pulse characteristic selected from the group consisting of pulse amplitude, pulse frequency, pulse width, pulse waveform, pulse waveform, and pulse phase.

3. A method as in claim 2, wherein the step of causing the electrical signals to be changed further comprises causing the pulse characteristic to be changed between the two or more means for outputting.

4. A method as in claim 1, wherein the electrical signal comprises a pulse train, and wherein the step of causing the electrical signals to be changed further comprises causing a pulse train characteristic of the electrical signal to be changed, the pulse train characteristic selected from the group consisting of burst amplitude, burst waveform, burst frequency, and burst width.

5. A method as in claim 4, wherein the step of causing the electrical signals to be changed further comprises causing the pulse train characteristic to be changed between the two or more means for outputting.

6. A method as in claim 1, wherein providing a baroreceptor activation device comprises providing an extravascular baroreceptor activation device.

7. A method as in claim 1, wherein providing a baroreceptor activation device comprises providing an intravascular baroreceptor activation device.

8. A method as in claim 1, wherein providing a baroreceptor activation device including two or more means for each outputting an electrical signal comprises providing a baroreceptor activation device including two or more contact points on a single electrode.

9. A method as in claim 1, wherein causing the electrical signals of the at least two means for each outputting to be changed relative to one another comprises alternating the electrical signals among the at least two means for each outputting.

10. A system for inducing a baroreceptor signal to effect a change in the baroreflex system in a patient, the system comprising:

a baroreceptor activation device including a first means for outputting adapted to be implanted proximate a first baroreceptor location, and a second means for outputting adapted to be positioned proximate a second baroreceptor location, such that activation of the baroreceptor activation device induces a baroreceptor signal in the patient; and a control system connected to the baroreceptor activation device, the control system including a processor and a memory, wherein the memory includes software defining a stimulus regimen, the control system generating a control signal that activates one of the first means for outputting or the second means for outputting of the baroreceptor activation device as a function of the stimulus regimen, the stimulus regimen causing the control signal to be changed to promote long term efficacy of inducing baroreceptor signals and reduce exposure of a single baroreceptor location by alternating the control signal between the first means for outputting and the second means for outputting.

11. A system as in claim 10, wherein the baroreceptor activation device comprises an extravascular baroreceptor activation device.

12. A system as in claim 10, wherein the baroreceptor activation device comprises an intravascular baroreceptor activation device.

13. A system as in claim 10, wherein the stimulus regimen is configured to cause the control signal to be changed to promote long term efficacy of inducing baroreceptor signals by alternating the control signal among the at least two means for outputting.

14. A method of inducing a baroreceptor signal to effect a change in the baroreflex system in a patient, the method comprising the steps of:
providing a baroreceptor activation device including a first means for outputting an electrical signal to electrically induce a baroreceptor signal and a second means for outputting an electrical signal to electrically induce a baroreceptor signal, providing instructions for operating the baroreflex activation device, comprising:
implanting the baroreceptor activation device such that the first means for outputting an electrical signal is proximate a first baroreceptor location in the patient and the second means for outputting an electrical signal is proximate a second baroreceptor location;
alternating the electrical signal between the first means for outputting and the second means for outputting to promote long term efficacy of inducing baroreceptor signals and reduce exposure of a single baroreceptor location.

15. A method as in claim 14, wherein implanting the baroreceptor activation device comprises implanting the baroreceptor activation device on or about the exterior of a blood vessel.

16. A method as in claim 14, wherein implanting the baroreceptor activation device comprises implanting the baroreceptor activation device within a blood vessel.

* * * * *